(12) United States Patent
Fischer et al.

(10) Patent No.: US 7,141,533 B2
(45) Date of Patent: Nov. 28, 2006

(54) HETARYL-SUBSTITUTED HETEROCYCLES

(75) Inventors: Reiner Fischer, Monheim (DE);
Thomas Bretschneider, Lohmar (DE);
Axel Trautwein, Bergisch Gladbach
(DE); Astrid Ullmann, Köln (DE);
Mark Wilhelm Drewes, Langenfeld
(DE); Christoph Erdelen, Leichlingen
(DE); Peter Dahmen, Neuss (DE);
Dieter Feucht, Monheim (DE); **Rolf
Pontzen**, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 129 days.

(21) Appl. No.: 10/850,679

(22) Filed: May 21, 2004

(65) Prior Publication Data

US 2004/0220243 A1    Nov. 4, 2004

Related U.S. Application Data

(62) Division of application No. 10/297,873, filed as application No. PCT/EP01/06174 on May 31, 2001, now Pat. No. 6,767,864.

(30) Foreign Application Priority Data

Jun. 13, 2000    (DE) ............................. 100 29 077

(51) Int. Cl.
*A01N 43/78*    (2006.01)
*C07D 277/22*    (2006.01)

(52) U.S. Cl. .................. 504/266; 514/365; 514/369; 548/187; 548/204

(58) Field of Classification Search ............... 548/204; 514/365
See application file for complete search history.

(56) References Cited

U.S. PATENT DOCUMENTS

| | | | |
|---|---|---|---|
| 3,538,107 A | 11/1970 | Hepworth et al. | 260/302 |
| 3,749,787 A | 7/1973 | Hepworth et al. | 424/270 |
| 4,296,237 A | 10/1981 | Cragoe, Jr. | 544/405 |
| 4,298,743 A | 11/1981 | Cragoe, Jr. et al. | 548/203 |
| 4,377,588 A | 3/1983 | Cragoe, Jr. et al. | 424/270 |
| 4,379,791 A | 4/1983 | Cragoe, Jr. et al. | 424/270 |
| 4,725,610 A | 2/1988 | Meguro et al. | 514/369 |
| 5,075,316 A * | 12/1991 | Hubele | 514/275 |
| 5,084,083 A | 1/1992 | Lewis et al. | 71/90 |
| 5,728,720 A | 3/1998 | Shinkai | 514/374 |
| 5,939,445 A | 8/1999 | Shinkai | 514/374 |
| 6,037,359 A | 3/2000 | Shinkai | 514/374 |
| 6,057,343 A | 5/2000 | Shinkai | 514/340 |
| 6,160,124 A | 12/2000 | Shinkai | 548/236 |

FOREIGN PATENT DOCUMENTS

| | | |
|---|---|---|
| EP | 0 017 850 | 10/1980 |
| EP | 0 389 699 | 5/1994 |
| WO | 87/03807 | 7/1987 |
| WO | 99/32464 | 7/1999 |
| WO | WO 99/32464 * | 7/1999 |

OTHER PUBLICATIONS

J. Med. Chem., (month unavailable) 1983, 26, pp. 700-714, Inhibitors of Glycolic Acid Oxidase. 4-Substituted 3-Hydroxy-1H-pyrrole-2,5-dione Derivatives by C. S. Rooney et al.

Journal of Molecular Structure, 366, (month unavailable) 1996, pp. 131-137, Investigation of the relationship between the inhibitory activity of glycolic acid oxidase (GAO) and its chemical structure: electron-topological approach. by Y. Güzel.

Chemical Reviews, vol. 52, (month unavailable) 1953, pp. 237-416, by Norman O. V. Sonntag.

Indian J. Chem., 6, (month unavailable) 1968, Isoquinoline Derivatives: Part XVIII—Formation of 1-Alkyl-(or alkaryl of aryl)-3-methyl-7-chloro-(or 5-chloro)-isoquinolines. B. Bhattacharaya.

Chemistry and Industry, Nov. 9, 1968, (London), p. 1568, Use of molecular sieves in the methyl esterification of carboxylic acids by H. R. Harrison et al.

Organikum, VEB Deutscher Verlag der Wissenschafsen Berlin, (month unavailable) 1977, pp. 505-507, Reaktionen von Carbonsäuren und Carbonsäurederivaten mit Basen.

Houben-Weyl. Methods of Organic Chemistry, vol. 8, (month unavailable) 1952, H. Henecka, pp. 467-469, Umwandlung von Carbonsäuren—Carbonsäurehalogenide.

J. Med. Chem., (month unavailable) 1996, 39, pp. 237-245, Azole Phenoxy Hydroxyureas as Selective and Orally Active Inhibitors of 5-Lipoxygenase by M. S. Malamas et al.

J. Med. Chem., (month unavailable) 1998, 41, pp. 5037-5054, N-(2-Benzoylphenyl-L-tyrosine PPARγ Agonists. 2. Structure-Activity Relationship and Optimization of the Phenyl Alkyl Ether Moiety by J. L. Collins et al.

Chem. Pharm. Bull., vol. 34, (month unavailable) 1986, pp. 2840-2851, Studies of Antidiabetic Agents. VII.[1)] Synthesis and Hypoglycemic Activity of 4-Oxazoleacetic Acid Derivatives[2)] by K. Meguro et al.

(Continued)

*Primary Examiner*—Kamal A. Saeed
*Assistant Examiner*—Andrew B. Freistein
(74) *Attorney, Agent, or Firm*—Richard E. L. Henderson

(57) ABSTRACT

The present invention relates to novel compounds of the formula (I)

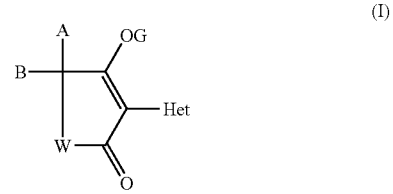

in which A, B, W, G and Het are each as defined in the description, to a plurality of processes for their preparation and to their use as pesticides and herbicides.

11 Claims, No Drawings

OTHER PUBLICATIONS

Chem. Pharm. Bull., vol. 36, (month unavailable) 1988, pp. 4435-4440, Synthesis of 5-Alkyl-4-oxazoleacetic Acid Derivatives with Hypolipidemic Activities by M. Seki et al.

Can. J. Chem., 53, (month unavailable) 1975, pp. 3339-3350, Stereochemistry of the Bucherer-Bergs and Strecker Reactions of 4-tert-Butylcyclohexanone by J. T. Edward and C. Jitrangsri.

J. Chem. Soc., (month unavailable) 1961, pp. 4372-4379, Amino-acids of the Cyclohexane Series. Part I. by L. Munday.

J. Med. Chem. (month unavailable) 1992, 35, pp. 1853-1864, Novel Thiazolidine-2,4-diones as Potent Euglycemic Agents by B. Hulin et al.

* cited by examiner

HETARYL-SUBSTITUTED HETEROCYCLES

This application is a divisional of U.S. application Ser. No. 10/297,873, filed Dec. 10, 2002 now U.S. Pat. No. 6,767,864, which was filed under 35 U.S.C. 371 as a national stage application of International Applicational No. PCT/EP01/06174, filed May 31, 2001, which was published in German as International Patent Publication WO 01/96333 on Dec. 20, 2001, which is entitled to the right of priority of German Patent Application No. 100 29 077.9, filed Jun. 13, 2000.

The present invention relates to novel hetaryl-substituted heterocycles, to a plurality of processes for their preparation and to their use as pesticides and herbicides.

4-Thiazolyl-3-hydroxy-3-pyrroline-2,5-diones are known as glycolic acid oxidase inhibitors; U.S. Pat. Nos. 4,296,237; 4,377,588; EP-A-025 232; Rooney C. S. et al., J. Med. Chem. 26 700–714 (1983); Guzel Y. et al. THEOCHEM 366 131–137 (1996).

The present invention provides novel compounds of the formula (I)

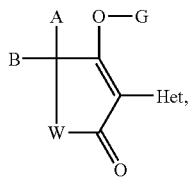
(I)

in which

W represents N-D$^{(1)}$, oxygen$^{(2)}$ or sulphur$^{(3)}$,

Het represents in each case optionally substituted thiazolyl, oxazolyl or pyrazolyl, A represents hydrogen, in each case optionally halogen-substituted alkyl, alkenyl, alkoxyalkyl, polyalkoxyalkyl, alkylthioalkyl, saturated or unsaturated optionally substituted cycloalkyl in which optionally at least one ring atom is replaced by a heteroatom, or in each case optionally halogen-, alkyl-, halogenoalkyl, alkoxy-, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or represents an optionally substituted radical from the group consisting of alkyl, alkenyl, alkinyl, alkoxyalkyl, polyalkoxyalkyl, alkylthioalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which is unsubstituted or substituted in the A,D moiety and optionally contains at least one heteroatom, G represents hydrogen (a) or represents one of the groups

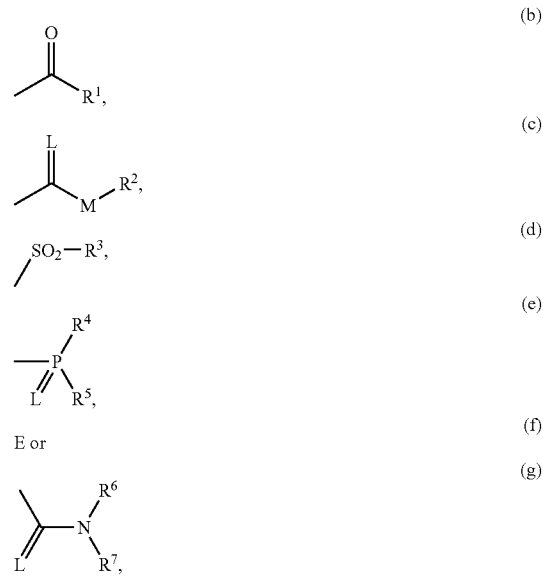

in which

E represents a metal ion equivalent or an ammonium ion,

L represents oxygen or sulphur,

M represents oxygen or sulphur,

R$^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, R$^2$ represents in each case optionally halogen-substituted alkyl, alkenyl, alkoxyalkyl, polyalkoxyalkyl or represents in each case optionally substituted cycloalkyl, phenyl or benzyl, R$^3$ represents alkyl, halogenoalkyl or represents in each case optionally substituted phenyl or benzyl, R$^4$ and R$^5$ independently of one another each represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, R$^6$ and R$^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures in varying composition which may, if desired, be separated in a customary manner. The present invention provides both the pure isomers and the isomer mixtures, their preparation and use, and compositions comprising them. However, hereinbelow, compounds of the formula (I) are always referred to for the sake of simplicity, although what is meant are both the pure compounds and, if appropriate, also mixtures with varying proportions of isomeric compounds.

Including W=N-D[(1)], oxygen[(2)] or sulphur[(3)], the following principal structures (I-1) to (I-3) result:

(I-1)
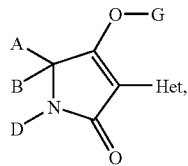

(I-2)
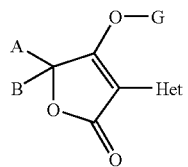

(I-3)
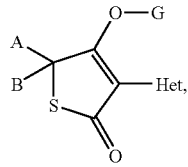

in which
A, B, D and G are each as defined above and
Het represents thiazolyl or oxazolyl.

Including the various meanings of Het, the following principal structures result:
(I-1-A) to (I-3-B) if W represents N-D[(1)], oxygen[(2)] or sulphur[(3)]

(I-1-A):
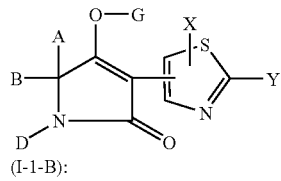

(I-1-B):
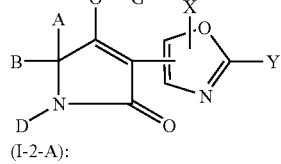

(I-2-A):
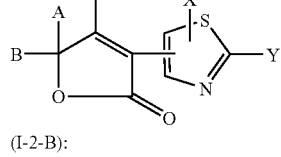

(I-2-B):
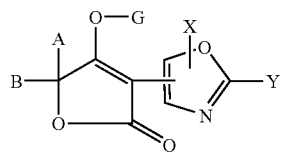

(I-3-A):
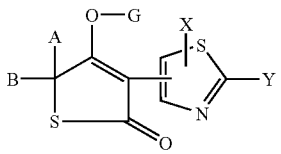

(I-3-B):
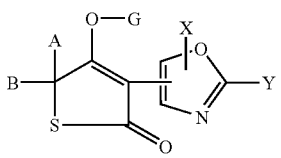

in which
A, B, D and G are each as defined above and
X represents hydrogen, halogen, alkyl, halogenoalkyl, alkoxy, halogenoalkoxy, alkenyloxy, haloalkenyloxy, nitro, cyano or optionally substituted phenyl,
Y represents halogen, alkyl, halogenoalkyl, alkoxy, halogenoalkoxy, alkenyloxy, alkylthio, alkylsulphinyl, alkylsulphoxinyl, alkylsulphonyl or represents in each case optionally substituted phenyl, benzyl, phenoxy or phenylthio.

Including the various meanings (a), (b), (c), (d), (e), (f) and (g) of the group G, the following principal structures (I-1-A-a) to (I-1-A-g) result if W represents N-D[(1)]

(I-1-A-a):
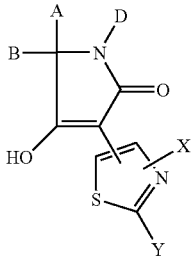

(I-1-A-b):
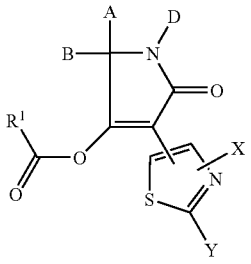

-continued
(I-1-A-c):
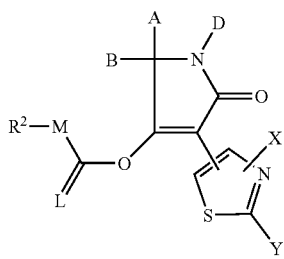
(I-1-A-d):
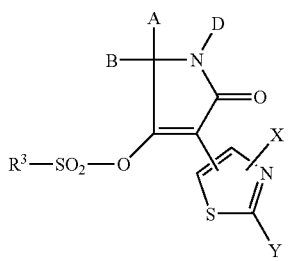
(I-1-A-e):
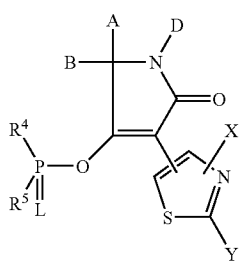
(I-1-A-f):
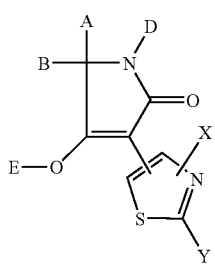
(I-1-A-g):
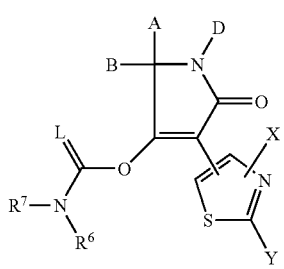
in which
A, B, D, E, L, M, X, Y, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-1-B-a) to (I-1-B-g) result if W represents N-D$^{(1)}$
(I-1-B-a):
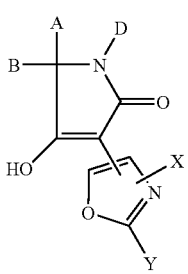
(I-1-B-b):
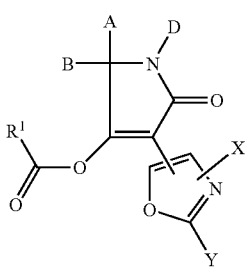
(I-1-B-c):
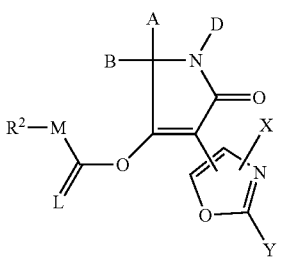
(I-1-B-d):
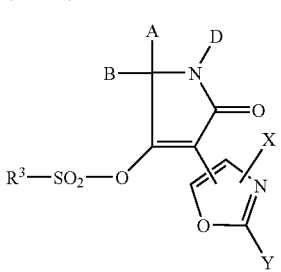

(I-1-B-e):

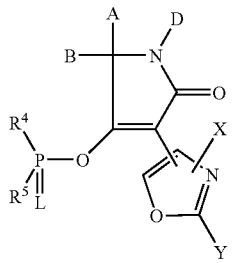

(I-1-B-f):

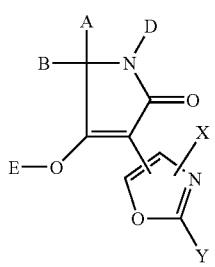

(I-1-B-g):

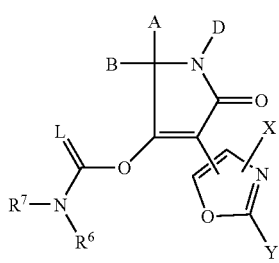

in which
A, B, D, E, L, M, X, Y, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-2-A-a) to (I-2-A-g) result if W represents oxygen$^{(2)}$ (I-2-A-a):

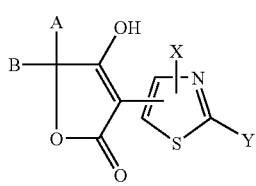

(I-2-A-b):

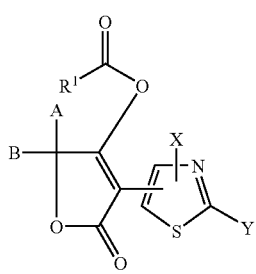

(I-2-A-c):

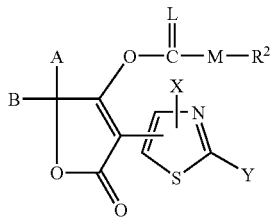

(I-2-A-d):

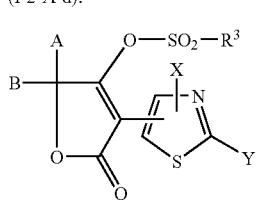

(I-2-A-e):

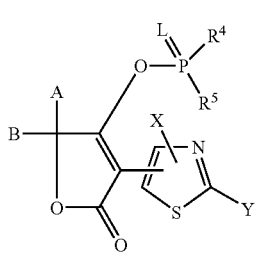

(I-2-A-f):

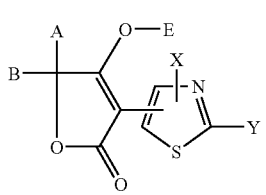

(I-2-A-g):

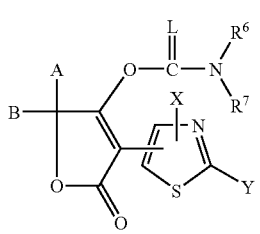

in which
A, B, E, L, M, X, Y, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-2-B-a) to (I-2-B-g) result if W represents oxygen$^{(2)}$ (I-2-B-a):
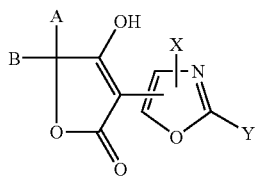
(I-2-B-b):
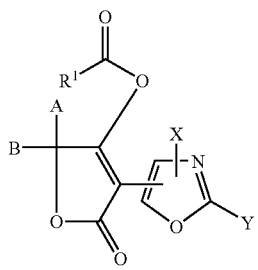
(I-2-B-c):
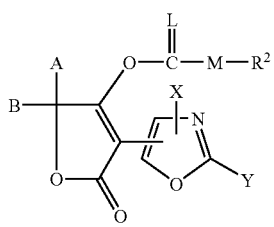
(I-2-B-d):
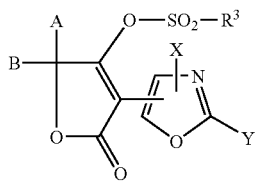
(I-2-B-e):
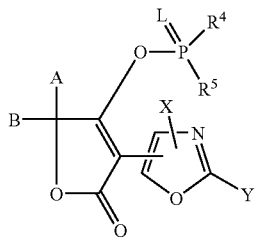
(I-2-B-f):
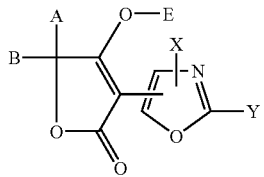
(I-2-B-g):
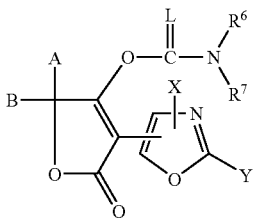
in which
A, B, E, L, M, X, Y, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-3-A-a) to (I-3-A-g) result if W represents sulphur[(3)]
(I-3-A-a):
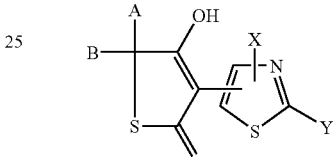
(I-3-A-b):
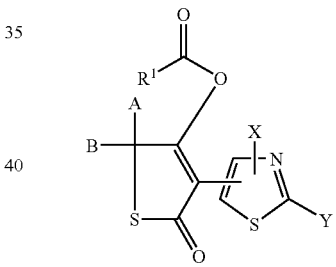
(I-3-A-c):
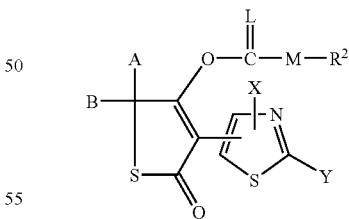
(I-3-A-d):
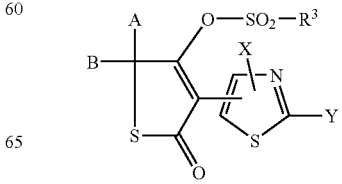

-continued (I-3-A-e):
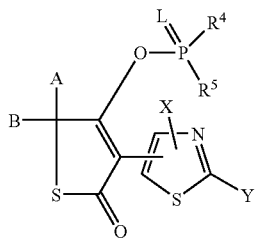

(I-3-A-f):
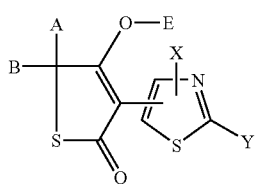

(I-3-A-g):
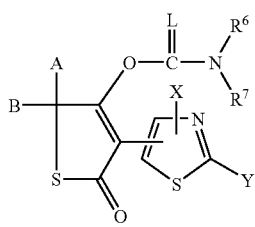

in which
A, B, E, L, M, X, Y, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-B-a) to (I-3-B-g) result if W represents sulphur[(3)]

(I-3-B-a):
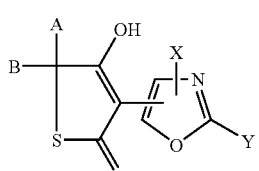

(I-3-B-b):
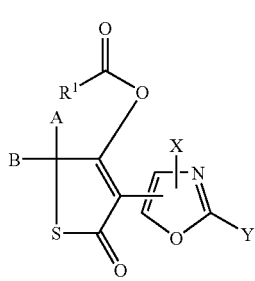

(I-3-B-c):
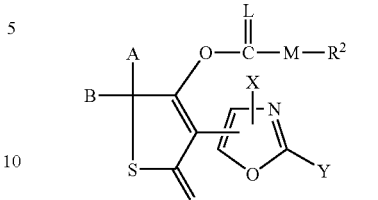

(I-3-B-d):
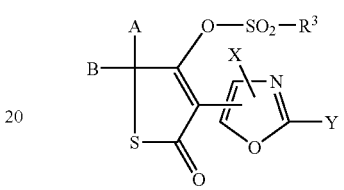

(I-3-B-e):
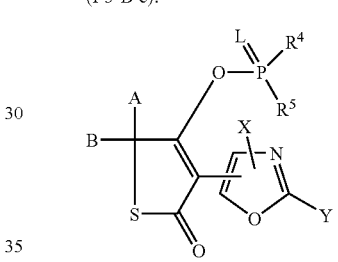

(I-3-B-f):
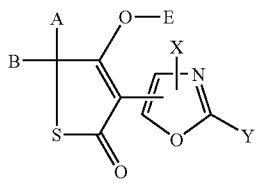

(I-3-B-g):
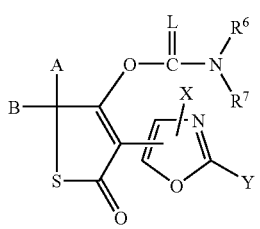

in which
A, B, E, L, M, X, Y, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Substituted 3-hetaryl-pyrrolidine-2,4-diones or enols thereof of the formulae (I-1-A-a) to (I-1-B-a)

(I-1-A-a) to (I-1-B-a)

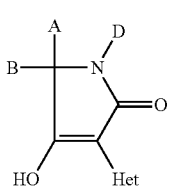

in which
A, B, D and Het are each as defined above
are obtained when
N-acylamino acid esters of the formula (II)

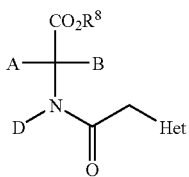

(II)

in which
A, B, D and Het are each as defined above
and
$R^8$ represents alkyl (preferably $C_1$–$C_6$-alkyl)
are condensed intramolecularly in the presence of a diluent and in the presence of a base.

(B) Moreover, it has been found that substituted 3-hetaryl-4-hydroxy-$\Delta^3$-di-hydrofuranone derivatives of the formulae (I-2-A-a) to (I-2-B-a)

(I-2-A-a) to (I-2-B-a)

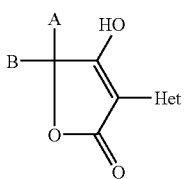

in which
A, B and Het are each as defined above
are obtained when
carboxylic esters of the formula (III)

(III)

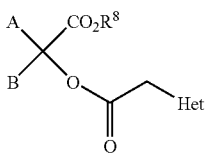

in which
A, B, Het and $R^8$ are each as defined above
are condensed intramolecularly in the presence of a diluent and in the presence of a base.

(C) Furthermore, it has been found that substituted 3-hetaryl-4-hydroxy-$\Delta^3$-di-hydrothiophene-2-one derivatives of the formulae (I-3-A-a) to (I-3-B-a)

(I-3-A-a) to (I-3-B-a)

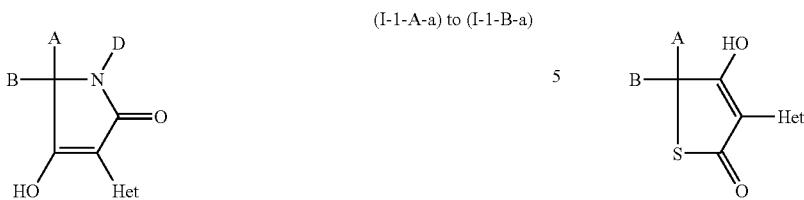

in which
A, B and Het are each as defined above
are obtained when
β-ketocarboxylic esters of the formula (IV)

(IV)

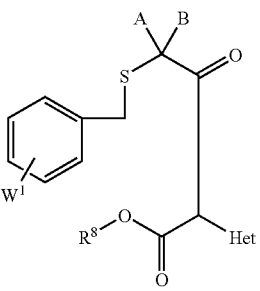

in which
A, B, Het and $R^8$ are each as defined above and
$W^1$ represents hydrogen, halogen, alkyl (preferably $C_1$–$C_6$-alkyl) or alkoxy (preferably $C_1$–$C_8$-alkoxy)
are cyclized intramolecularly, if appropriate in the presence of a diluent and in the presence of an acid.

Moreover, it has been found
(D) that the compounds of the formulae (I-1-A-b) to (I-3-B-b) shown above, in which A, B, D, $R^1$ and Het are each as defined above, are obtained when compounds of the formulae (I-1-A-a) to (I-3-B-a) shown above, in which A, B, D and Het are each as defined above, are in each case reacted
(α) with acyl halides of the formula (V)

(V)

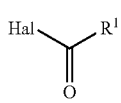

in which
$R^1$ is as defined above and
Hal represents halogen (in particular chlorine or bromine)
or
(β) with carboxylic anhydrides of the formula (VI)

$R^1$—CO—O—CO—$R^1$ (VI)

in which
$R^1$ is as defined above,
if appropriate in the presence of a diluent and if appropriate in the presence of an acid binder;
(E) that the compounds of the formulae (I-1-A-c) to (I-3-B-c) shown above, in which A, B, D, $R^2$, M and Het are each as defined above and L represents oxygen, are obtained when compounds of the formulae (I-1-A-a) to (I-3-B-a) shown above, in which A B, D and Het are each as defined above, are in each case reacted
with chloroformic esters or chloroformic thioesters of the formula (VII)

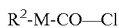  (VII)

in which
R² and M are each as defined above,
if appropriate in the presence of a diluent and if appropriate in the presence of an acid binder;

(F) that the compounds of the formulae (I-1-A-c) to (I-3-B-c) shown above, in which A, B, D, R², M and Het are each as defined above and L represents sulphur, are obtained when compounds of the formulae (I-1-A-a) to (I-3-B-a) shown above, in which A, B, D and Het are each as defined above, are in each case reacted
with chloromonothioformic esters or chlorodithioformic esters of the formula (VIII)

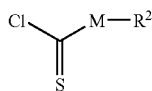  (VIII)

in which
M and R² are each as defined above,
if appropriate in the presence of a diluent and if appropriate in the presence of an acid binder,
and (G) that compounds of the formulae (I-1-A-d) to (I-3-B-d) shown above, in which A, B, D, R³ and Het are each as defined above, are obtained when compounds of the formulae (I-1-A-a) to (I-3-B-a) shown above, in which A, B, D and Het are each as defined above, are in each case reacted
with sulphonyl chlorides of the formula (IX)

  (IX)

in which
R³ is as defined above,
if appropriate in the presence of a diluent and if appropriate in the presence of an acid binder, (H) that compounds of the formulae (I-1-A-e) to (I-3-B-e) shown above, in which A, B, D, L, R⁴, R⁵ and Het are each as defined above, are obtained when compounds of the formulae (I-1-A-a) to (I-3-B-a) shown above, in which A, B, D and Het are each as defined above, are in each case reacted
with phosphorous compounds of the formula (X)

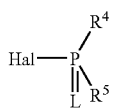  (X)

in which
L, R⁴ and R⁵ are each as defined above and
Hal represents halogen (in particular chlorine or bromine),
if appropriate in the presence of a diluent and if appropriate in the presence of an acid binder, (I) that compounds of the formulae (I-1-A-f) to (I-3-B-f) shown above, in which A, B, D, E and Het are each as defined above, are obtained when compounds of the formulae (I-1-A-a) to (I-3-B-a), in which A, B, D and Het are each as defined above, are in each case reacted
with metal compounds or amines of the formula (XI) or (XII)

$$Me(OR^{10})_t$$  (XI)

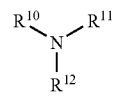  (XII)

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another each represent hydrogen or alkyl (preferably $C_1$–$C_8$-alkyl),
if appropriate in the presence of a diluent, (J) that compounds of the formulae (I-1-A-g) to (I-3-B-g) shown above, in which A, B, D, L, R⁶, R⁷ and Het are each as defined above, are obtained when compounds of the formulae (I-1-A-a) to (I-3-B-a) shown above, in which A, B, D and Het are each as defined above, are in each case reacted (α) with isocyanates or isothiocyanates of the formula (XIII)

$$R^6-N=C=L$$  (XIII)

in which
R⁶ and L are each as defined above,
if appropriate in the presence of a diluent and if appropriate in the presence of a catalyst, or (β) with carbamoyl chlorides or thiocarbamoyl chlorides of the formula (XIV)

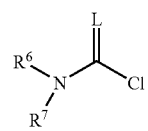  (XIV)

in which
L, R⁶ and R⁷ are each as defined above,
if appropriate in the presence of a diluent and if appropriate in the presence of an acid binder.

Furthermore, it has been found that the novel compounds of the formula (I) are highly active as pesticides, preferably as insecticides, acaricides and herbicides.

The formula (I) provides a general definition of the compounds according to the invention. Preferred substituents or ranges of the radicals listed in the formulae mentioned above and below are illustrated below:

Het preferably represents

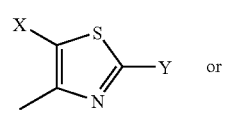  (A)

or

-continued

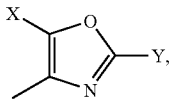

(B)

X preferably represents hydrogen, halogen, $C_1$–$C_6$-alkyl, $C_1$–$C_4$-halogenoalkyl, $C_1$–$C_6$-alkoxy, $C_3$–$C_6$-alkenyloxy, nitro or cyano, Y preferably represents halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, $C_1$–$C_6$-alkylsulphonyl, $C_1$–$C_6$-alkylsulphoxinyl or represents the group

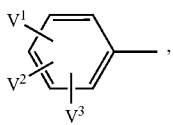

or in the case of Het=thiazolyl ((I-1-A) to (I-3-A)) also represents

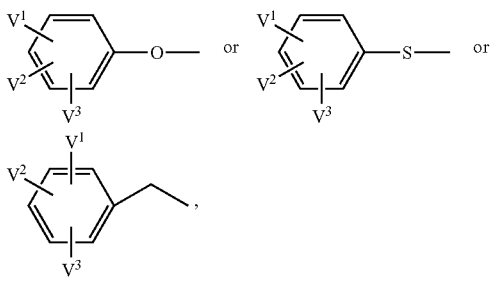

$V^1$ preferably represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano, phenoxy or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, $V^2$ and $V^3$ independently of one another each preferably represent hydrogen, halogen, $C_1$–$C_6$-alkyl, $C_1$–$C_6$-alkoxy, $C_1$–$C_4$-halogenoalkyl or $C_1$–$C_4$-halogenoalkoxy, $V^1$ and $V^2$ together with the carbon atoms to which they are attached preferably represent an optionally $C_1$–$C_4$-alkyl- or halogen-substituted saturated or unsaturated 5- or 6-membered cycle in which optionally one to three carbon atoms may be replaced by oxygen, sulphur or nitrogen, W preferably represents N-D$^{(1)}$, oxygen$^{(2)}$ or sulphur$^{(3)}$, A preferably represents hydrogen or in each case optionally fluorine- or chlorine-substituted $C_1$–$C_{12}$-alkyl, $C_3$–$C_8$-alkenyl, $C_1$–$C_6$-alkoxy-$C_1$–$C_6$-alkyl, poly-$C_1$–$C_6$-alkoxy-$C_1$–$C_6$-alkyl, $C_1$–$C_{10}$-alkylthio-$C_1$–$C_6$-alkyl, optionally fluorine-, chlorine-, $C_1$–$C_6$-alkyl- or $C_1$–$C_6$-alkoxy-substituted $C_3$–$C_8$-cycloalkyl in which optionally one or two not directly adjacent ring members are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl (phenyl or naphthyl), hetaryl having 5 or 6 ring atoms (for example furanyl, pyridyl, imidazolyl, triazolyl, pyrazolyl, pyrimidyl, thiazolyl or thienyl) or $C_6$- or $C_{10}$-aryl-$C_1$–$C_6$-alkyl (phenyl-$C_1$–$C_6$-alkyl or naphthyl-$C_1$–$C_6$-alkyl), B preferably represents hydrogen, $C_1$–$C_6$-alkyl or $C_1$–$C_4$-alkoxy-$C_1$–$C_4$-alkly, or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_6$-alkyl, $C_3$–$C_8$-cycloalkyl, $C_1$–$C_4$-halogenoalkyl, $C_1$–$C_6$-alkoxy, $C_1$–$C_6$-alkylthio, halogen or phenyl or A, B and the carbon atom to which they are attached preferably represent $C_5$–$C_6$-cycloalkyl which is substituted by an alkylenediyl group which optionally contains an oxygen or sulphur atom, or by an alkylenedioxyl or by an alkylenedithioyl group which, together with the carbon atom to which it is attached, forms a further five- or six-membered ring which may optionally be mono- to tetrasubstituted by $C_1$–$C_4$-alkyl, or A, B and the carbon atom to which they are attached preferably represent $C_3$–$C_8$-cycloalkyl or $C_5$–$C_8$-cycloalkenyl in which two substituents together with the carbon atoms to which they are attached represent in each case optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur, D preferably represents hydrogen, in each case optionally halogen- or cyano-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur or in each case optionally halogen-, $C_1$–$C_6$-alkyl-, $C_1$–$C_6$-halogenoalkyl, $C_1$–$C_6$-alkoxy-, $C_1$–$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$–$C_6$-alkyl or hetaryl-$C_1$–$C_6$-alkyl having 5 or 6 ring atoms (for example furanyl, imidazolyl, pyridyl, thiazolyl, pyrazolyl, pyrimidyl, pyrrolyl, thienyl or triazolyl), or A and D together preferably represent in each case optionally substituted $C_3$–$C_6$-alkanediyl or $C_3$–$C_6$-alkenediyl in which optionally one methylene group is replaced by a carbonyl group, oxygen or sulphur, possible substituents being in each case:

halogen, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl grouping, $C_3$–$C_6$-alkenediyl grouping or a butadienyl grouping which is optionally substituted by $C_1$–$C_6$-alkyl or in which optionally two adjacent substituents together with the carbon atoms to which they are attached form a further saturated or unsaturated cycle having 5 or 6 ring atoms (in the case of the compounds of the formula (I-1-A) to (I-1-B), A and D together with the atoms to which they are attached in this case represent, for example, the groups AD-1 to AD-10 mentioned further below) which may contain oxygen or sulphur, or which optionally contains one of the groups below

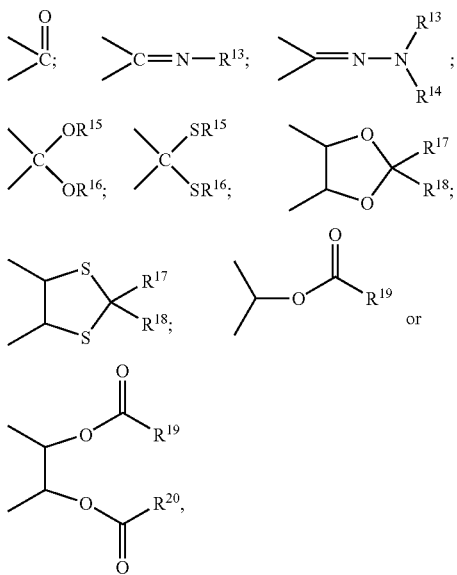

G preferably represents hydrogen (a) or represents one of the groups

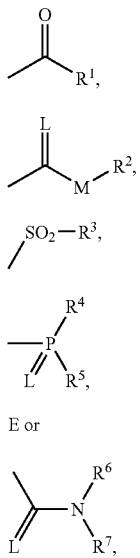

in which

E represents a metal ion equivalent or an ammonium ion,

L represents oxygen or sulphur and

M represents oxygen or sulphur, $R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably not more than two) not directly adjacent ring members are replaced by oxygen and/or sulphur, represents optionally halogen-, cyano-, nitro-, $C_1$–$C_6$-alkyl, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen-, $C_1$–$C_6$-alkyl-, $C_1$–$C_2$-halogenoalkyl- or $C_1$–$C_4$-alkoxy-substituted 5- or 6-membered hetaryl (for example pyrazolyl, thiazolyl, pyridyl, pyrimidyl, furanyl or thienyl), represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl), $R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl or $C_1$–$C_6$-alkoxy-substituted $C_3$–$C_8$-cycloalkyl in which optionally one ring atom is replaced by oxygen, or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another each preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-Alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio, $R^6$ and $R^7$ independently of one another each preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one carbon atom is replaced by oxygen or sulphur, $R^{13}$ preferably represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl, in which optionally one methylene group is replaced by oxygen or sulphur, or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^{14}$ preferably represents hydrogen or $C_1$–$C_8$-alkyl or $R^{13}$ and $R^{14}$ together preferably represent $C_4$–$C_6$-alkanediyl, $R^{15}$ and $R^{16}$ are identical or different and each preferably represent $C_1$–$C_6$-alkyl or $R^{15}$ and $R^{16}$ together preferably represent a $C_2$–$C_4$-alkanediyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl, $R^{17}$ and $R^{18}$ independently of one another each preferably represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl or $R^{17}$ and $R^{18}$ together with the carbon atom to which they are attached preferably represent a carbonyl group or represent optionally halogen-, $C_1$–$C_4$-alkyl or $C_1$–$C_4$-alkoxy-substituted $C_5$–$C_7$-cycloalkyl in which optionally one methylene group is replaced by oxygen or sulphur, $R^{19}$ and $R^{20}$ independently of one another each preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

In the radical definitions mentioned as being preferred, halogen represents fluorine, chlorine, bromine and iodine, in particular fluorine, chlorine and bromine.

Het particularly preferably represents

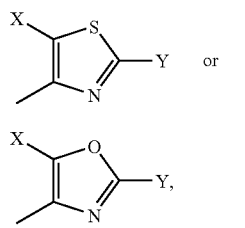

X particularly preferably represents hydrogen, chlorine, bromine, $C_1$–$C_4$-alkyl, $C_1$–$C_2$-halogenoalkyl, nitro or cyano, Y particularly preferably represents chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-alkylsulphonyl or represents the group

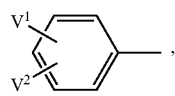

or in the case of Het=thiazolyl ((I-1-A) to (I-3-A)) also represents

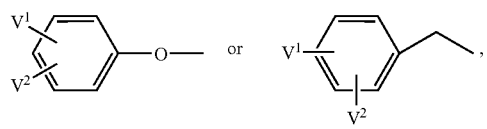

$V^1$ particularly preferably represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenoalkoxy, nitro, cyano, phenoxy or represents phenyl, phenoxy, phenoxy-$C_1$–$C_2$-alkyl, phenyl-$C_1$–$C_2$-alkoxy, phenylthio-$C_1$–$C_2$-alkyl or phenyl-$C_1$–$C_2$-alkylthio, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, $V^2$ particularly preferably represents hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, or $V^1$ and $V^2$ together with the carbon atoms to which they are attached particularly preferably represent an optionally fluorine- or methyl-substituted 5- or 6-membered cycle in which optionally one or two carbon atoms may be replaced by oxygen, W particularly preferably represents N-D$^{(1)}$, oxygen$^{(2)}$ or sulphur$^{(3)}$, A particularly preferably represents hydrogen, in each case optionally fluorine-substituted $C_1$–$C_{10}$-alkyl, $C_1$–$C_4$-alkoxy-$C_1$–$C_4$-alkyl, optionally fluorine-, chlorine-, $C_1$–$C_4$-alkyl- or $C_1$–$C_4$-alkoxy-substituted $C_3$–$C_7$-cycloalkyl in which optionally one ring member is replaced by oxygen or sulphur or in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_2$-alkyl, B particularly preferably represents hydrogen or $C_1$–$C_4$-alkyl, or A, B and the carbon atom to which they are attached particularly preferably represent saturated $C_5$–$C_7$-cycloalkyl in which optionally one ring member is replaced by oxygen or sulphur and which is optionally mono- or disubstituted by $C_1$–$C_6$-alkyl, $C_5$–$C_6$-cycloalkyl, $C_1$–$C_2$-halogenoalkyl, $C_1$–$C_6$-alkoxy, fluorine, chlorine or phenyl or A, B and the carbon atom to which they are attached particularly preferably represent $C_5$–$C_6$-cycloalkyl which is substituted by an alkylenediyl group which optionally contains an oxygen or sulphur atom or by an alkylenedioxyl or by an alkylenedithioyl group which together with the carbon atom to which it is attached forms a further five- or six-membered ring which may optionally be mono- to trisubstituted by $C_1$–$C_3$-alkyl, or A, B and the carbon atom to which they are attached particularly preferably represent $C_5$–$C_6$-cycloalkyl or $C_5$–$C_6$-cycloalkenyl in which two substituents together with the carbon atoms to which they are attached represent in each case optionally $C_1$–$C_5$-alkyl-, $C_1$–$C_5$-alkoxy-, fluorine-, chlorine- or bromine-substituted $C_2$–$C_4$-alkanediyl, $C_2$–$C_4$-alkenediyl in which optionally one methylene group is replaced by oxygen or sulphur or represent butadienediyl, D particularly preferably represents hydrogen, represents in each case optionally fluorine-substituted $C_1$–$C_{10}$-alkyl, $C_3$–$C_6$-alkenyl, $C_1$–$C_6$-alkoxy-$C_2$–$C_4$-alkyl or $C_1$–$C_6$-alkylthio-$C_2$–$C_4$-alkyl, represents optionally fluorine-, $C_1$–$C_4$-alkyl, $C_1$–$C_4$-alkoxy or $C_1$–$C_2$-halogenoalkyl-substituted $C_3$–$C_7$-cycloalkyl, in which optionally one methylene group is replaced by oxygen or sulphur or represents in each case optionally fluorine-, chlorine-, bromine-, $C_1$–$C_4$-alkyl-, $C_1$–$C_2$-halogenoalkyl-, $C_1$–$C_4$-alkoxy- or $C_1$–$C_2$-halogenoalkoxy-substituted phenyl or phenyl-$C_1$–$C_4$-alkyl, or A and D together particularly preferably represent optionally substituted $C_3$–$C_5$-alkanediyl in which optionally one methylene group may be replaced by a carbonyl group, oxygen or sulphur, possible substituents being hydroxyl, $C_1$–$C_6$-alkyl or $C_1$–$C_4$-alkoxy, or A and D together with the atoms to which they are attached particularly preferably represent one of the groups AD-1 to AD-10:

AD-1 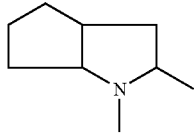

AD-2 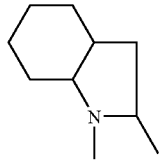

AD-3 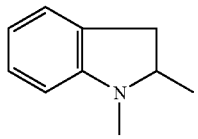

AD-4 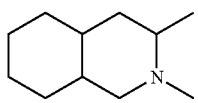

AD-5 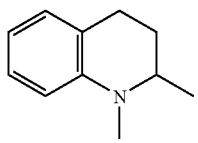

AD-6 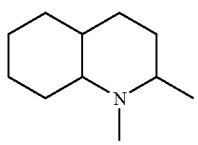

AD-7 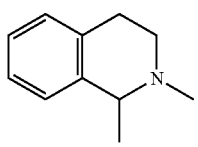

AD-8 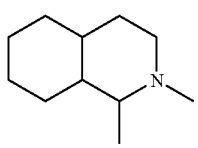

AD-9 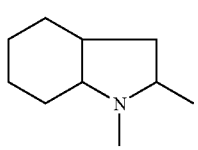

AD-10 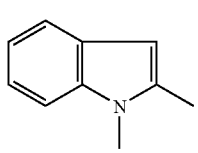

G particularly preferably represents hydrogen (a) or represents one of the groups

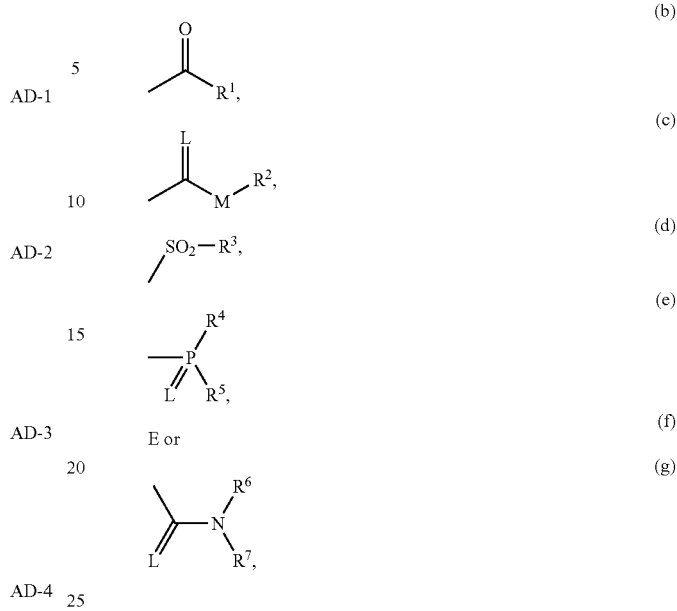

in particular (a), (b), (c) or (g),
in which
E represents a metal ion equivalent or an ammonium ion,
L represents oxygen or sulphur and
M represents oxygen or sulphur, $R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_4$-alkyl, $C_1$–$C_6$-alkylthio-$C_1$–$C_4$-alkyl or optionally fluorine-, chlorine-, $C_1$–$C_5$-alkyl- or $C_1$–$C_5$-alkoxy-substituted $C_3$–$C_7$-cycloalkyl in which optionally one or two not directly adjacent ring members are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine-, bromine-, $C_1$–$C_4$-alkyl-, trifluoromethyl- or $C_1$–$C_2$-alkoxy-substituted pyrazolyl, thiazolyl, pyridyl, pyrimidyl, furanyl or thienyl, $R^2$ particularly preferably represents in each case optionally fluorine-substituted $C_1$–$C_{16}$-alkyl, $C_2$–$C_{16}$-alkenyl or $C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, $C_1$–$C_2$-halogenoalkyl- or $C_1$–$C_2$-halogenoalkoxy-substituted phenyl or benzyl, $R^3$ particularly preferably represents optionally fluorine-substituted $C_1$–$C_6$-alkyl or represents optionally fluorine-, chlorine-, bromine-, $C_1$–$C_4$-alkyl-, $C_1$–$C_4$-alkoxy-, $C_1$–$C_3$-halogenoalkyl-, $C_1$–$C_3$-halogenoalkoxy-, cyano- or nitro-substituted phenyl, $R^4$ particularly preferably represents $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represents in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio, $R^5$ particularly preferably represents $C_1$–$C_6$-alkoxy or $C_1$–$C_6$-alkylthio, $R^6$ particularly preferably represents $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represents optionally fluorine-, chlorine-, bromine-, $C_1$–$C_3$-halogenoalkyl-, $C_1$–$C_4$-alkyl- or $C_1$–$C_4$-alkoxy-substituted phenyl, represents optionally fluorine-, chlorine-, bromine-, $C_1$–$C_4$-alkyl-, $C_1$–$C_3$-halogenoalkyl- or $C_1$–$C_4$-alkoxy-substituted benzyl, $R^7$ particularly preferably represents hydrogen, $C_1$–$C_6$-alkyl, $C_3$–$C_6$-alkenyl, or $R^6$ and $R^7$ together particularly preferably represent an optionally methyl- or ethyl-substituted $C_4$–$C_5$-alkylene radical in which optionally one methylene group is replaced by oxygen or sulphur.

In the radical definitions mentioned as being particularly preferred, halogen represents fluorine, chlorine, bromine and iodine, in particular fluorine, chlorine and bromine.

Het very particularly preferably represents

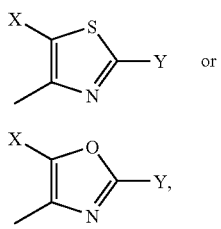

X very particularly preferably represents hydrogen, chlorine, bromine, methyl, ethyl, n-propyl, iso-propyl, n-butyl or iso-butyl, Y very particularly preferably represents methyl, ethyl, n-propyl, i-propyl, n-butyl, i-butyl, tert-butyl, trifluoromethyl or represents the group

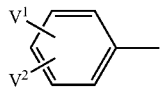

or in the case of Het=thiazolyl ((I-1-A) to (I-3-A)) also represents

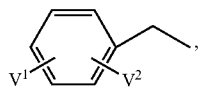

$V^1$ very particularly preferably represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano, phenoxy or phenyl which is optionally mono- or disubstituted by fluorine, chlorine, methyl, methoxy, trifluoromethyl or trifluoromethoxy, $V^2$ very particularly preferably represents hydrogen, fluorine, chlorine, methyl, ethyl, n-propyl, iso-propyl, methoxy, ethoxy, trifluoromethyl or trifluoromethoxy, or $V^1$ and $V^2$ together very particularly preferably represent —O—$CH_2$—O—, —O—$CF_2$—O— or —O—$CF_2$—$CF_2$—O—, W very particularly preferably represents N-D$^{(1)}$, oxygen$^{(2)}$ or sulphur$^{(3)}$, A very particularly preferably represents hydrogen, represents in each case optionally fluorine-substituted $C_1$–$C_8$-alkyl or $C_1$–$C_4$-alkoxy-$C_1$–$C_2$-alkyl, optionally fluorine-, methyl-, ethyl- or methoxy-substituted $C_3$–$C_6$-cycloalkyl in which optionally one ring member is replaced by oxygen or sulphur or represents in each case optionally fluorine-, chlorine-, bromine-, methyl-, ethyl-, n-propyl-, iso-propyl-, tert-butyl-, methoxy-, ethoxy-, trifluoromethyl-, trifluoromethoxy-, cyano- or nitro-substituted phenyl or benzyl, B very particularly preferably represents hydrogen, methyl or ethyl, or A, B and the carbon atom to which they are attached very particularly preferably represent saturated $C_5$–$C_6$-cycloalkyl in which optionally one ring member is replaced by oxygen or sulphur and which is optionally mono- or disubstituted by methyl, ethyl, propyl, isopropyl, butyl, isobutyl, sec-butyl, tert-butyl, trifluoromethyl, methoxy, ethoxy, propoxy, iso-propoxy, butoxy or iso-butoxy or A, B and the carbon atom to which they are attached very particularly preferably represent $C_6$-cycloalkyl which is substituted by an alkylenedioxyl group which is optionally mono- or disubstituted by methyl or ethyl and which together with the carbon atom to which it is attached forms a further five- or six-membered ring or A, B and the carbon atom to which they are attached very particularly preferably represent $C_5$–$C_6$-cycloalkyl or $C_5$–$C_6$-cycloalkenyl in which two substituents together with the carbon atoms to which they are attached represent $C_2$–$C_4$-alkanediyl or $C_2$–$C_4$-alkenediyl in which in each case optionally one methylene group is replaced by oxygen or sulphur, or represent butadienediyl, D very particularly preferably represents hydrogen, represents in each case optionally fluorine-substituted $C_1$–$C_6$-alkyl, $C_3$–$C_4$-alkenyl, $C_1$–$C_4$-alkoxy-$C_2$–$C_3$-alkyl, $C_1$–$C_4$-alkylthio-$C_2$–$C_3$-alkyl or $C_3$–$C_6$-cycloalkyl in which optionally one methylene group is replaced by oxygen or sulphur or represents in each case optionally fluorine-, chlorine-, methyl-, ethyl-, n-propyl-, iso-propyl-, methoxy-, ethoxy-, trifluoromethyl- or trifluoromethoxy-substituted phenyl or benzyl, or A and D together very particularly preferably represent optionally substituted $C_3$–$C_4$-alkanediyl in which optionally one carbon atom is replaced by oxygen or sulphur and which is optionally substituted by methyl or A and D together with the atoms to which they are attached very particularly preferably represent one of the groups AD below:

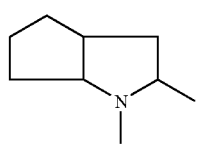

AD-1

-continued

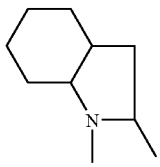
AD-2

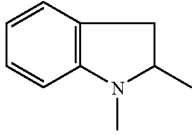
AD-3

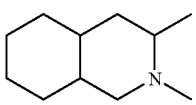
AD-4

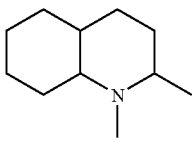
AD-6

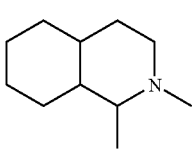
AD-8

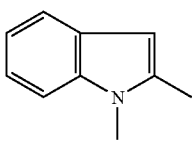
AD-10

G very particularly preferably represents hydrogen (a) or represents one of the groups

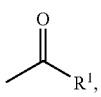
(b)

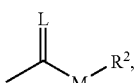
(c)

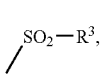
(d)

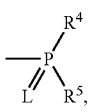
E or
(e)
(f)
(g)

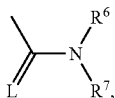

in particular (a), (b) or (c), in which
E represents a metal ion equivalent or an ammonium ion,
L represents oxygen or sulphur and
M represents oxygen or sulphur, $R^1$ very particularly preferably represents in each case optionally fluorine-substituted $C_1$–$C_{14}$-alkyl, $C_2$–$C_{14}$-alkenyl, $C_1$–$C_4$-alkoxy-$C_1$–$C_2$-alkyl, $C_1$–$C_4$-alkylthio-$C_1$–$C_2$-alkyl or in each case optionally fluorine-, chlorine-, methyl-, ethyl- or methoxy-substituted cyclopropyl, cyclopentyl or cyclohexyl, represents phenyl which is optionally mono- or disubstituted by fluorine, chlorine, bromine, cyano, nitro, methyl, ethyl, tert-butyl, methoxy, ethoxy, trifluoromethyl or trifluoromethoxy, represents thienyl or pyridyl, each of which is optionally monosubstituted by fluorine, chlorine, bromine or methyl, $R^2$ very particularly preferably represents in each case optionally fluorine-substituted $C_1$–$C_8$-alkyl, $C_2$–$C_8$-alkenyl or $C_1$–$C_4$-alkoxy-$C_2$–$C_3$-alkyl, represents optionally fluorine-, chlorine-, methyl-, ethyl-, n-propyl-, iso-propyl- or methoxy-substituted cyclohexyl, or represents in each case optionally fluorine-, chlorine-, cyano-, nitro-, methyl-, ethyl-, methoxy-, trifluoromethyl- or trifluoromethoxy-substituted phenyl or benzyl, $R^3$ very particularly preferably represents methyl, ethyl, n-propyl or represents phenyl which is optionally monosubstituted by fluorine, chlorine, bromine, methyl, tert-butyl, methoxy, trifluoromethyl, trifluoromethoxy, cyano or nitro, $R^4$ very particularly preferably represents $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represents in each case optionally fluorine-, chlorine-, bromine-, nitro-, cyano-, $C_1$–$C_2$-alkoxy-, $C_1$–$C_2$-fluoroalkoxy-, $C_1$–$C_2$-alkylthio-, $C_1$–$C_2$-fluoroalkylthio- or $C_1$–$C_3$-alkyl-substituted phenyl, phenoxy or phenylthio, $R^5$ very particularly preferably represents methoxy, ethoxy, methylthio or ethylthio, $R^6$ very particularly preferably represents $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represents optionally fluorine-, chlorine-, bromine-, trifluoromethyl-, methyl- or methoxy-substituted phenyl, represents optionally fluorine-, chlorine-, bromine-, methyl-, trifluoromethyl- or methoxy-substituted benzyl, $R^7$ very particularly preferably represents hydrogen, methyl, ethyl, propyl or allyl, or $R^6$ and $R^7$ together very particularly preferably represent a $C_5$–$C_6$-alkylene radical in which optionally one methylene group is replaced by oxygen or sulphur.

Het with particular preference represents (A)

(B)

X with particular preference represents hydrogen, chlorine, bromine, methyl, ethyl, n-propyl, or iso-propyl, Y with particular preference represents methyl, ethyl, n-propyl, i-propyl, n-butyl, i-butyl, tert-butyl, trifluoromethyl or represents the group

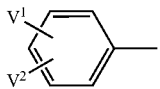

or in the case of Het=thiazolyl ((I-1-A) or (I-3-A)) also represents

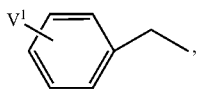

$V^1$ with particular preference represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, phenoxy, represents optionally chlorine- or trifluoromethyl-substituted phenyl, $V^2$ with particular preference represents hydrogen, fluorine, chlorine, methyl, ethyl, methoxy or trifluoromethyl, or $V^1$ and $V^2$ together with particular preference represent —O—CH$_2$—O— or —O—CF$_2$—O—, W with particular preference represents N-D$^{(1)}$, oxygen$^{(2)}$ or sulphur$^{(3)}$, A with particular preference represents hydrogen or $C_1$–$C_4$-alkyl or cyclopropyl, B with particular preference represents hydrogen or methyl, or A, B and the carbon atom to which they are attached with particular preference represent saturated $C_5$–$C_6$-cycloalkyl in which optionally one ring member is replaced by oxygen or sulphur, and which is optionally mono- or disubstituted by methyl, ethyl, propyl, isopropyl, trifluoromethyl, methoxy, ethoxy, propoxy, butoxy or iso-butoxy, or represents $C_5$–$C_6$-cycloalkyl in which two not directly adjacent carbon atoms form a further five-membered ring, D with particular preference represents hydrogen, D also with particular preference represents i-propyl, A and D together with the atoms to which they are attached with particular preference represent cyclohexyl in which one ring atom may be replaced by sulphur, G with particular preference represents hydrogen (a) or in the case of Het=thiazolyl ((I-1-A) to (I-3-A)) (represents) one of the groups

(b)

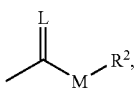

(c)

in which
L represents oxygen and
M represents oxygen, $R^1$ with particular preference represents in each case optionally fluorine- or chlorine-substituted $C_1$–$C_4$-alkyl, $C_2$–$C_4$-alkenyl, $C_1$–$C_4$-alkoxy-$C_1$–$C_2$-alkyl, $C_1$–$C_4$-alkylthio-$C_1$–$C_2$-alkyl or optionally fluorine-, chlorine-, methyl-, ethyl- or methoxy-substituted cyclopropyl or cyclohexyl,
represents phenyl which is optionally monosubstituted by fluorine, chlorine, bromine, cyano, nitro, methyl, ethyl, n-propyl, i-propyl, tert-butyl, methoxy, ethoxy, i-propoxy, tert-butoxy, trifluoromethyl or trifluoromethoxy,
represents thienyl or pyridyl, each of which is optionally monosubstituted by chlorine or methyl, $R^2$ with particular preference represents optionally in each case fluorine-substituted $C_1$–$C_4$-alkyl, $C_2$–$C_4$-alkenyl or $C_1$–$C_4$-alkoxy-$C_2$–$C_3$-alkyl,
represents optionally methyl-, ethyl-, n-propyl-, iso-propyl- or methoxy-substituted cyclohexyl,
or represents phenyl or benzyl, each of which is optionally monosubstituted by fluorine, chlorine, cyano, nitro, methyl, ethyl, methoxy, trifluoromethyl or trifluoromethoxy, Het especially preferably represents

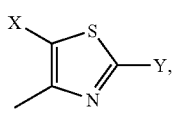
(A)

X especially preferably represents methyl, ethyl, n-propyl, i-propyl, chlorine or bromine, Y especially preferably represents methyl, ethyl, n-propyl or i-propyl or represents the groups

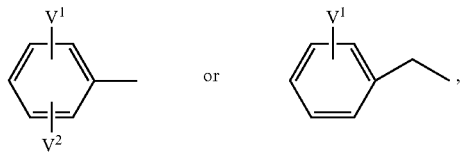

in which
$V^1$ especially preferably represents hydrogen, bromine, chlorine, methyl, trifluoromethyl, phenoxy or t-butyl or represents optionally chlorine- or trifluoromethyl-substituted phenyl,
$V^2$ especially preferably represents hydrogen, chlorine, fluorine or methoxy or
$V^1$ and $V^2$ together especially preferably represent —O—CH$_2$—O— or —O—CF$_2$—O—,
W especially preferably represents N-D$^{(1)}$, oxygen$^{(2)}$ or sulphur$^{(3)}$,
D especially preferably represents hydrogen or i-propyl (especially hydrogen),
A especially preferably represents methyl, ethyl, n- or i-propyl or cyclopropyl or hydrogen (especially methyl),
B especially preferably represents hydrogen or methyl, or
A and B and the carbon atom to which they are attached especially preferably represent cyclohexyl in which optionally one ring atom is replaced by oxygen and which is optionally mono- or disubstituted by methyl, ethyl, methoxy or ethoxy, or represent cyclohexyl in which two not directly adjacent carbon atoms form a further 5-membered C ring, A and D together with the atoms to which they are attached especially preferably represent cyclohexyl in which one ring atom may be replaced by sulphur, G especially preferably represents hydrogen (a) or represents one of the groups in which

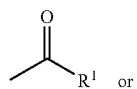
(b)

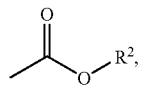
(c)

R¹ especially preferably represents methyl, ethyl, n-propyl or i-propyl or represents in each case optionally chlorine-substituted phenyl or pyridyl, R² especially preferably represents methyl, ethyl, phenyl, benzyl, n- or i-propyl.

Het especially preferably represents

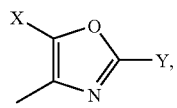
(B)

X especially preferably represents methyl or ethyl,

Y especially preferably represents optionally chlorine-substituted phenyl,

A especially preferably represents methyl, ethyl, n- or i-propyl,

B especially preferably represents methyl, or

A and B and the carbon atom to which they are attached together especially preferably represent cyclohexyl which is optionally substituted by methoxy or methyl, W especially preferably represents N-D or oxygen, D especially preferably represents hydrogen, G especially preferably represents hydrogen.

The abovementioned general or preferred radical definitions or illustrations can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Particular preference according to the invention is given to the compounds of the formula (I) which contain a combination of the meanings listed above as being with particular preference.

A special preference according to the invention is given to the compounds of the formula (I) which contain a combination of the meanings listed above as being especially preferred.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitutions, the substituents can be identical or different.

In addition to the compounds mentioned in the Preparation Examples, the following compounds of the formula (I-1-a) may, for example, be mentioned specifically:

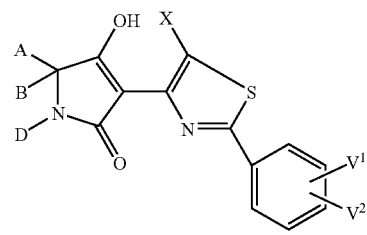

X=CH₃, V¹=3-Cl, V²=H.

TABLE 1

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| △ | CH₃ | H |
| ⬠ | CH₃ | H |
| ⬡ | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —CH₂—O—(CH₂)₃— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |

TABLE 1-continued

| A | B | D |
|---|---|---|
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
| —CH$_2$—CH—(CH$_2$)$_2$—CH— with —CH$_2$ bridge | | H |
| —CH$_2$—CH————CH—CH$_2$— with (CH$_2$)$_4$ bridge | | H |
| —CH$_2$—CH————CH—(CH$_2$)$_2$— with (CH$_2$)$_3$ bridge | | H |
| indane-fused | | H |
| tetralin-fused | | H |
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—S—CH$_2$— | | H |
| —CH$_2$—S—(CH$_2$)$_2$— | | H |
| —(CH$_2$)$_2$—S—CH$_2$— | | H |
| —CH$_2$—CH————CH— with (CH$_2$)$_3$ bridge | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |
| CH$_3$ | cyclohexyl | H |
| C$_2$H$_5$ | CH$_3$ | H |
| C$_2$H$_5$ | C$_2$H$_5$ | H |

TABLE 2

A, B and D are as stated in Table 1
X = CH$_3$; V$^1$ = 4-Cl; V$^2$ = H.

TABLE 3

A, B and D are as stated in Table 1
X = CH$_3$; V$^1$ = 3-CF$_3$; V$^2$ = H.

TABLE 4

A, B and D are as stated in Table 1
X = CH$_3$; V$^1$ = 4-CF$_3$; V$^2$ = H.

TABLE 5

A, B and D are as stated in Table 1
X = CH$_3$; V$^1$ = 4-Cl; V$^2$ = 2-Cl.

TABLE 6

A, B and D are as stated in Table 1
X = CH$_3$; V$^1$ = 4-Cl; V$^2$ = 3-Cl.

TABLE 7

A, B and D are as stated in Table 1
X = CH$_3$; V$^1$ = 4-CH$_3$; V$^2$ = H.

TABLE 8

A, B and D are as stated in Table 1
X = CH$_3$; V$^1$ = 2-Cl; V$^2$ = 6-OCH$_3$.

TABLE 9

A, B and D are as stated in Table 1
X = C$_2$H$_5$; V$^1$ = 4-Cl; V$^2$ = H.

TABLE 10

A, B and D are as stated in Table 1
X = C$_3$H$_7$; V$^1$ = 4-Cl; V$^2$ = H.

TABLE 11

A, B and D are as stated in Table 1
X = C$_2$H$_5$; V$^1$ = 3-Cl; V$^2$ = H

TABLE 12

A, B and D are as stated in Table 1
X = C$_3$H$_7$; V$^1$ = 3-Cl; V$^2$ = H.

TABLE 13

A, B and D are as stated in Table 1
X = C$_2$H$_5$; V$^1$ = 4-CF$_3$; V$^2$ = H.

TABLE 14

A, B and D are as stated in Table 1
X = C$_2$H$_5$; V$^1$ = 3-CF$_3$; V$^2$ = H.

TABLE 15

A, B and D are as stated in Table 1
X = C$_3$H$_7$; V$^1$ = 4-CF$_3$; V$^2$ = H.

TABLE 16

A, B and D are as stated in Table 1
X = C$_3$H$_7$; V$^1$ = 3-CF$_3$; V$^2$ = H.

TABLE 17

A, B and D are as stated in Table 1
X = Cl; V$^1$ = 4-Cl; V$^2$ = H.

TABLE 18

A, B and D are as stated in Table 1
X = Br; V$^1$ = 4-Cl; V$^2$ = H.

TABLE 19

A, B and D are as stated in Table 1
X = C$_2$H$_5$; V$^1$ = 3-Cl; V$^2$ = 4-Cl.

TABLE 20

A, B and D are as stated in Table 1
X = C$_3$H$_7$; V$^1$ = 3-Cl; V$^2$ = 4-Cl.

TABLE 21

A, B and D are as stated in Table 1
X = CH$_3$; V$^1$ = 4-Br; V$^2$ = H.

In addition to the compounds mentioned in the Preparation Examples, the following compounds of the formula (I-2-a) may, for example, be mentioned specifically:

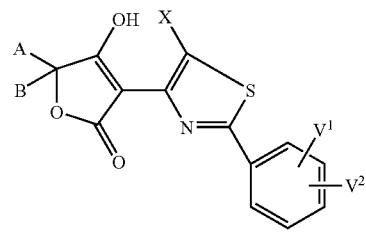

TABLE 22

X = CH$_3$, V$^1$ = 3-Cl, V$^2$ = H.

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
|  | CH$_3$ |
| 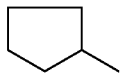 | CH$_3$ |
| 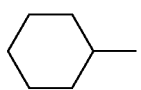 | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —CH$_2$—O—(CH$_2$)$_3$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |

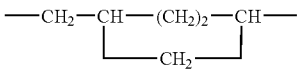

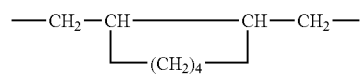

TABLE 22-continued $X = CH_3, V^1 = 3\text{-Cl}, V^2 = H.$

| A | B |
|---|---|
| 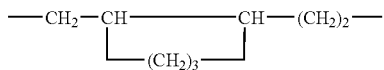 | |
| 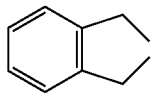 | |
| 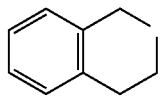 | |

TABLE 23

A and B are as stated in Table 22
$X = CH_3; V^1 = 4\text{-Cl}; V^2 = H.$

TABLE 24

A and B are as stated in Table 22
$X = CH_3; V^1 = 3\text{-CF}_3; V^2 = H.$

TABLE 25

A and B are as stated in Table 22
$X = CH_3; V^1 = 4\text{-CF}_3; V^2 = H.$

TABLE 26

A and B are as stated in Table 22
$X = CH_3; V^1 = 4\text{-Cl}; V^2 = 2\text{-Cl}.$

TABLE 27

A and B are as stated in Table 22
$X = CH_3; V^1 = 4\text{-Cl}; V^2 = 3\text{-Cl}.$

TABLE 28

A and B are as stated in Table 22
$X = CH_3; V^1 = 4\text{-CH}_3; V^2 = H.$

TABLE 29

A and B are as stated in Table 22
$X = CH_3; V^1 = 2\text{-Cl}; V^2 = 6\text{-OCH}_3.$

TABLE 30

A and B are as stated in Table 22
$X = C_2H_5; V^1 = 4\text{-Cl}; V^2 = H.$

TABLE 31

A and B are as stated in Table 22
$X = C_3H_7; V^1 = 4\text{-Cl}; V^2 = H.$

TABLE 32

A and B are as stated in Table 22
$X = C_2H_5; V^1 = 3\text{-Cl}; V^2 = H.$

TABLE 33

A and B are as stated in Table 22
$X = C_3H_7; V^1 = 3\text{-Cl}; V^2 = H.$

TABLE 34

A and B are as stated in Table 22
$X = C_2H_5; V^1 = 4\text{-CF}_3; V^2 = H$

TABLE 35

A and B are as stated in Table 22
$X = C_3H_7; V^1 = 4\text{-CF}_3; V^2 = H.$

TABLE 36

A and B are as stated in Table 22
$X = C_2H_5; V^1 = 3\text{-CF}_3; V^1 = H.$

TABLE 37

A and B are as stated in Table 22
$X = C_3H_7; V^1 = 3\text{-CF}_3; V^2 = H.$

TABLE 38

A and B are as stated in Table 22
$X = Cl; V^1 = 4\text{-Cl}; V^2 = H.$

TABLE 39

A and B are as stated in Table 22
$X = Br; V^1 = 4\text{-Cl}; V^2 = H.$

TABLE 40

A and B are as stated in Table 22
$X = C_2H_5; V^1 = 3\text{-Cl}; V^2 = 4\text{-Cl}.$

TABLE 41

A and B are as stated in Table 22
$X = C_3H_7; V^1 = 3\text{-Cl}; V^2 = 4\text{-Cl}.$

TABLE 42

A and B are as stated in Table 22
X = CH₃; V¹ = 4-Br; V² = H.

Using, according to process (A), ethyl N-[4-(5-methyl-2-phenyl)-thiazolylacetyl]-1-amino-cyclohexane-carboxylate as starting material, the course of the process according to the invention can be represented by the following equation:

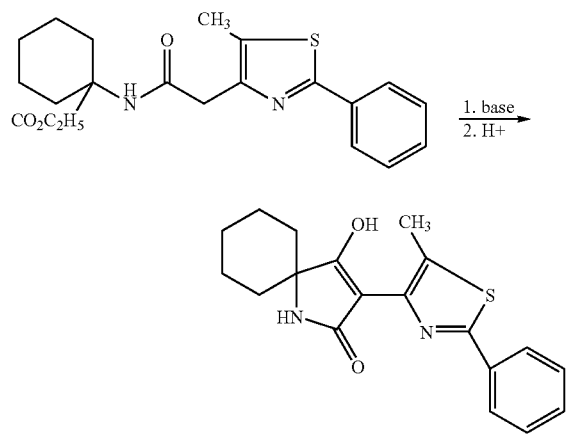

Using, according to process (B), ethyl O-[4-(5-methyl-2-(4-chloro)-phenyl)-thiazolyl-acetyl]-2-hydroxyisobutyrate as starting material, the course of the process according to the invention can be represented by the following equation:

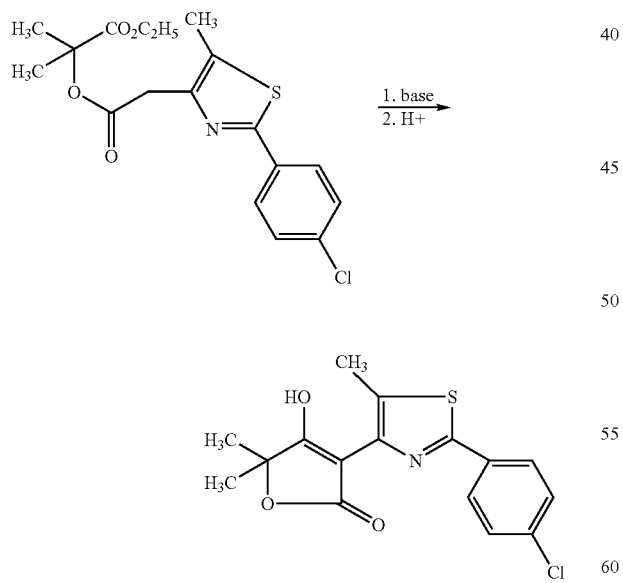

Using, according to process (C), ethyl 2-[4-(5-methyl-2-phenyl)-thiazolyl]-4-(4-methoxy)-benzylmercapto-4-methyl-3-oxo-valerate as starting material, the course of the process according to the invention can be represented by the following equation:

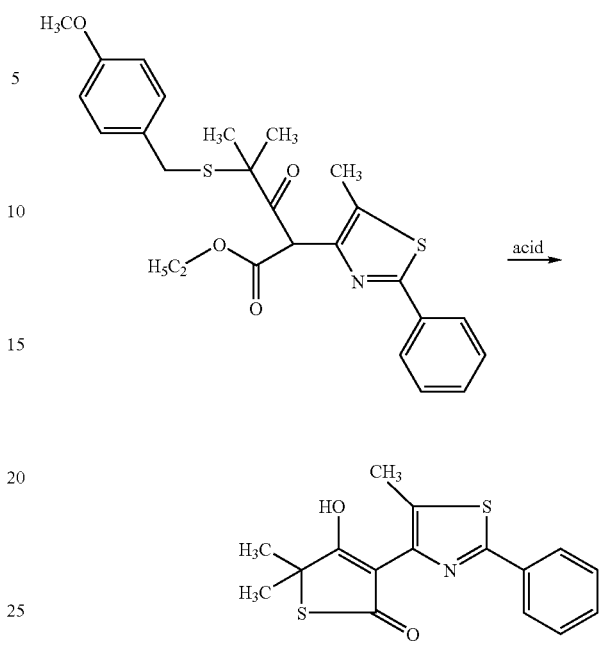

Using, according to process (Dα), 3-[4-(5-methyl-2-(3-chloro-phenyl)-thiazolyl]-5,5-dimethylpyrrolidine-2,4-dione and pivaloyl chloride as starting materials, the course of the process according to the invention can be represented by the following equation:

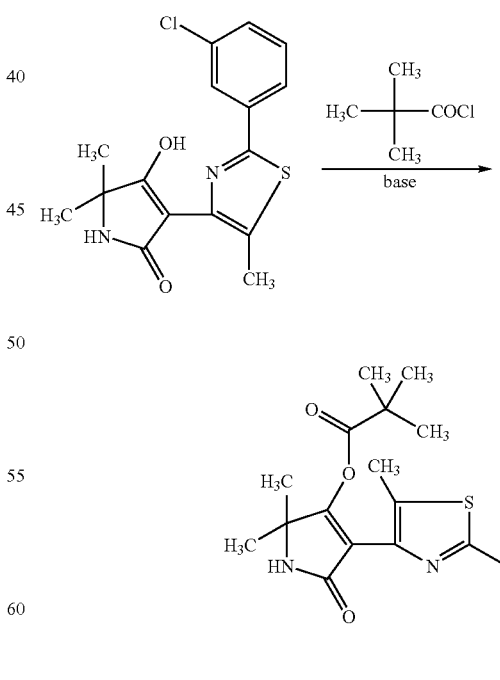

Using, according to process (Dβ), 3-[4-(5-ethyl-2-(4-methoxy-phenyl))-thiazoly]-4-hydroxy-5-phenyl-Δ³-dihydrofuran-2-one and acetic anhydride as starting materials, the course of the process according to the invention can be represented by the following equation:

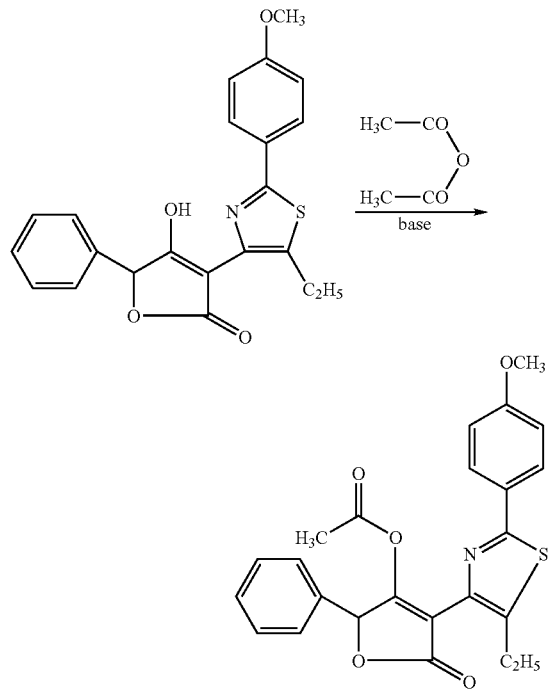

Using, according to process (E), 3-[4-(5-methyl-2-phenyl)-thiazolyl]-5,5-dimethylpyrrolidine-2,4-dione and ethoxyethyl chloroformate as starting materials, the course of the process according to the invention can be represented by the following equation:

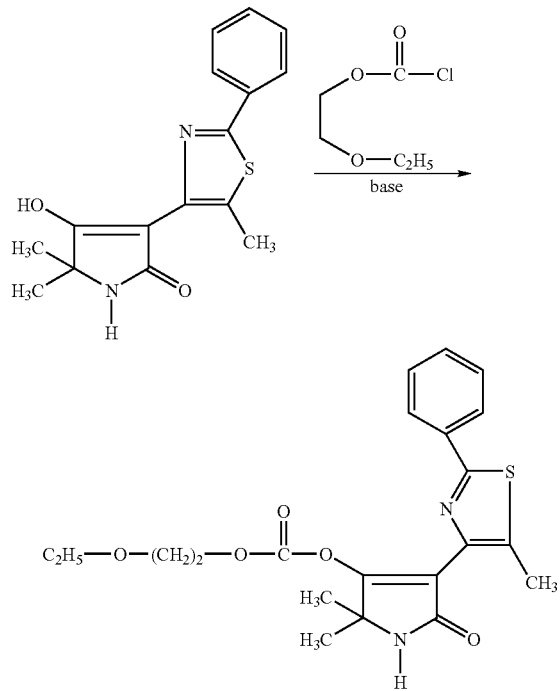

Using, according to process (F), 3-[4-(5-methyl-2-(4-fluoro-phenyl))-thiazolyl]-4-hydroxy-5,5-dimethyl-$\Delta^3$-dihydrofuran-2-one and methyl chloromonothioformate as starting materials, the course of the reaction can be represented as follows:

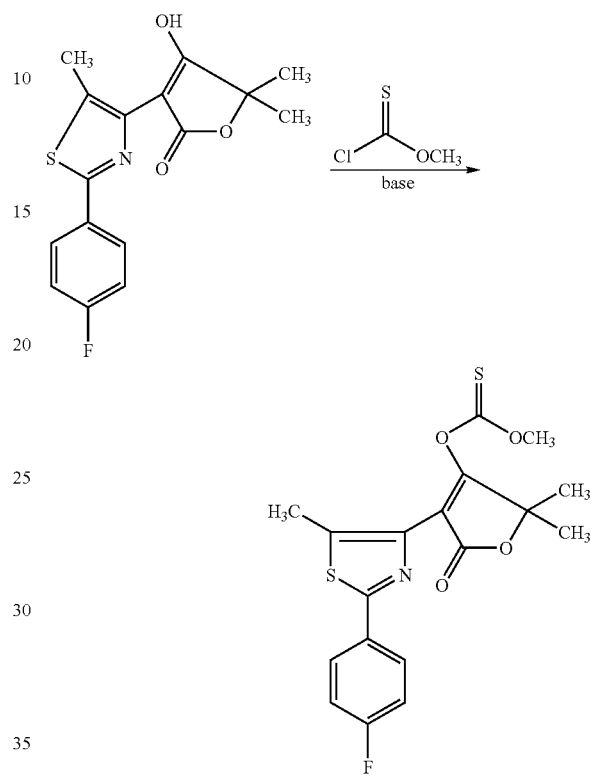

Using, according to process (G), 3-[4-(5-methyl-3-(4-methyl-phenyl))-thiazolyl]-5,5-pentamethylene-pyrrolidine-2,4-dione and methanesulphonyl chloride as starting materials, the course of the reaction can be represented by the following equation:

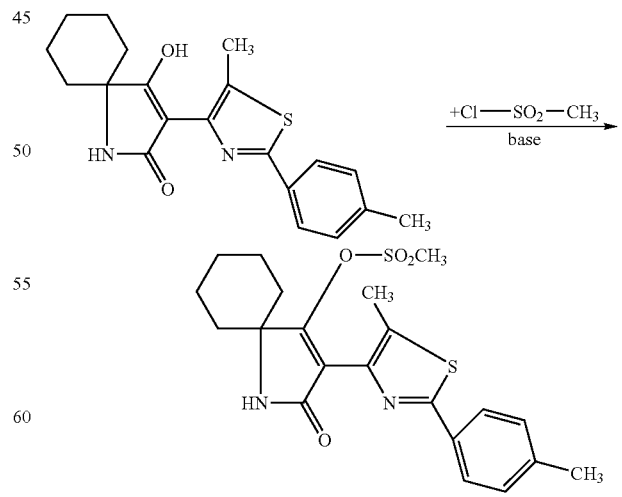

Using, according to process (H), 3-[4-(5-methyl-2-phenyl)-thiazolyl]-4-hydroxy-5,5-dimethyl-$\Delta^3$-dihydrofuran-2-one and 2,2,2-trifluoroethyl methanethio-phosphonyl chloride as starting materials, the course of the reaction can be represented by the following equation:

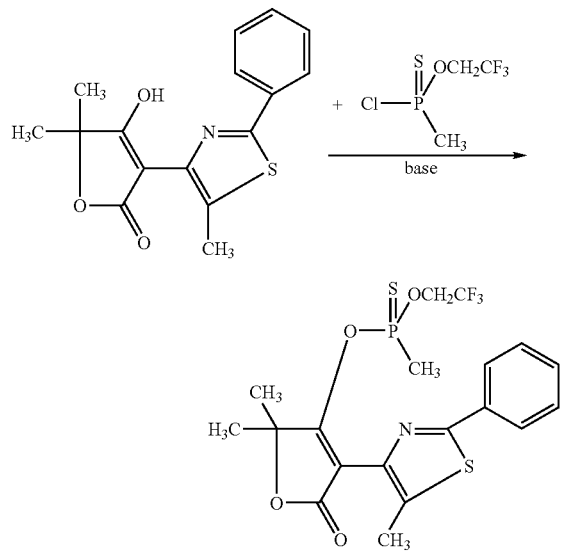

Using, according to process (I), 3-[4-(5-methyl-2-(4-trifluoromethyl-phenyl))-thiazolyl]-5-cyclopropyl-5-methyl-pyrrolidine-2,4-dione and NaOH as components, the course of the process according to the invention can be represented by the following equation:

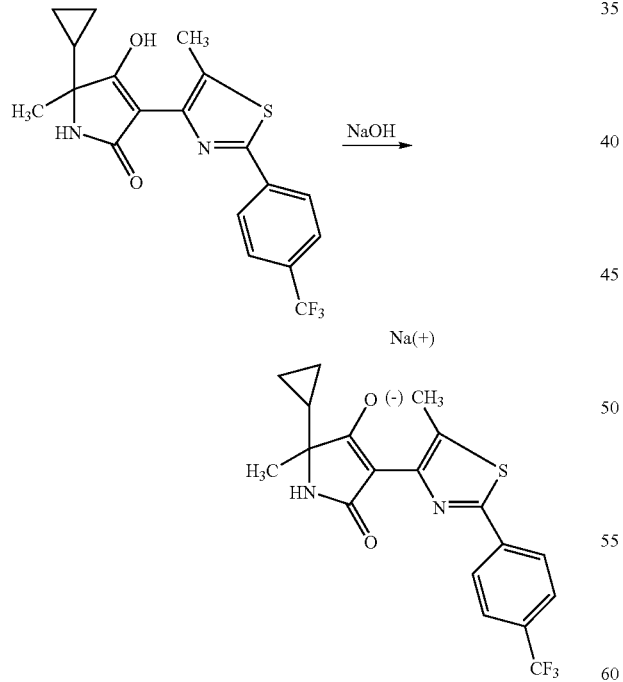

Using, according to process (Jα), 3-[4-(5-methyl-2-(3-trifluoromethyl-phenyl))-thiazolyl]-4-hydroxy-5-tetramethylene-Δ³-dihydro-furan-2-one and ethyl isocyanate as starting materials, the course of the reaction can be represented by the following equation:

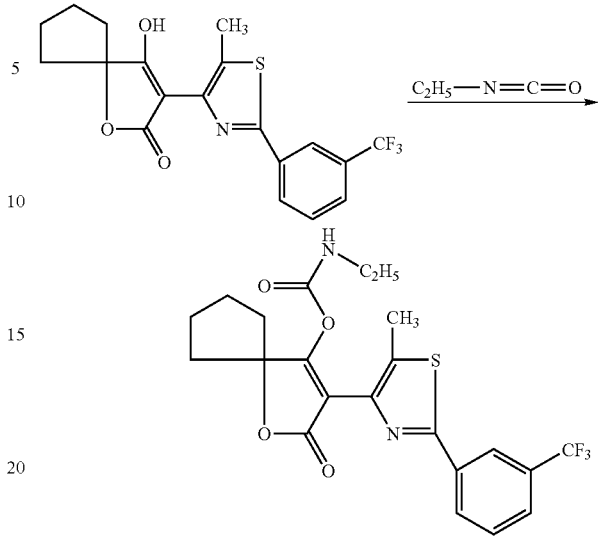

Using, according to process (Jβ), 3-[4-(5-methyl-2-phenyl)-thiazolyl]-5-methyl-pyrrolidine-2,4-dione and dimethylcarbamoyl chloride as starting materials, the course of the reaction can be represented by the following scheme:

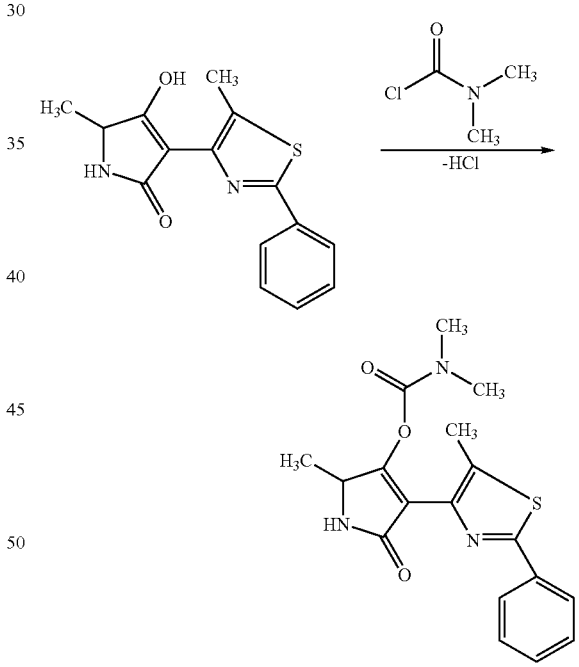

The compounds of the formula (II)

in which
A, B, D, Het and R⁸ are each as defined above required as starting materials in the process (a) according to the invention are novel.

The acylamino acid esters of the formula (II) are obtained, for example, when amino acid derivatives of the formula (XV)

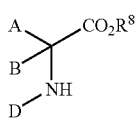
(XV)

in which
A, B, R⁸ and D are each as defined above are acylated with substituted hetarylacetic acid derivatives of the formula (XVI)

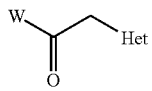
(XVI)

in which
Het is as defined above and
W represents a leaving group introduced by reagents for activating carboxylic acids, such as carbonyldiimidazole, carbonyldiimides (such as, for example, dicyclohexylcarbodiimide), phosphorylating agents (such as, for example, POCl₃, BOP-Cl), halogenating agents, for example thionyl chloride, oxalyl chloride, phosgene or chloroformic esters (Chem. Reviews 52, 237–416 (1953); Bhattacharya, Indian J. Chem. 6, 341–5, 1968)

or when acylamino acids of the formula (XVII)

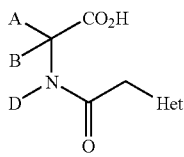
(XVII)

in which
A, B, D and Het are each as defined above are esterified (Chem. Ind. (London) 1568 (1968)).

The compounds of the formula (XVII)

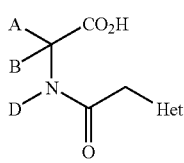
(XVII)

in which
A, B, D and Het are each as defined above are novel.

The compounds of the formula (XVII) are obtained when amino acids of the formula (XVIII)

(XVIII)

in which
A, B and D are each as defined above are acylated with substituted hetarylacetic acid derivatives of the formula (XVI)

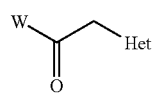
(XVI)

in which
W and Het are each as defined above, for example according to Schotten-Baumann (Organikum, VEB Deutscher Verlag der Wissenschaften, Berlin 1977, p. 505).

Some of the compounds of the formula (XVI) are novel. They can be prepared by processes known in principle (see, for example, H. Henecka, Houben-Weyl, Methoden der Organischen Chemie [Methods of Organic Chemistry], vol. 8, pp. 467–469 (1952)).

The compounds of the formula (XVI) are obtained, for example, by reacting substituted hetarylacetic acids of the formula (XIX)

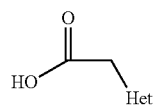
(XIX)

in which
X and Y are each as defined above with halogenating agents (for example thionyl chloride, thionyl bromide, oxalyl chloride, phosgene, phosphorous trichloride, phosphorous tribromide or phosphorous pentachloride), if appropriate in the presence of a diluent (for example optionally chlorinated aliphatic or aromatic hydrocarbons, such as toluene or methylene chloride) at temperatures of from −20° C. to 150° C., preferably from −10° C. to 100° C.

Some of the hetarylacetic acids of the formula (XIX) are commercially available, some are known, or they can be prepared by processes known in principle
a) thiazolylacetic acids: C. S. Rooney et al. J. Med. Chem. 26, 700–714 (1983); EP-A-368 592; M. S. Malamas et al. J. Med. Chem. 39, 237–246 (1996); J. L. Collins et al. J. Med. Chem. 41, 5037–5054 (1998); NL-A-66 14 130;
b) Oxazolylacetic acids: K. Meguro et al., Chem. Pharm. Bull, 34, 2840–2851 (1986), M. Sehi et al., Chem. Pharm. Bull. 36, 4435–4440 (1988), Malmas et al., J. Med. Chem. 39, 237–245 (1996), EP 0 177 353 A2, WO 87/03 807, WO 95/18 125, B. Hulin, J. Med. Chem. 35, 1853–1864 (1992), EP 0 389 699 A 1.

Some of the compounds of the formulae (XV) and (XVIII) are commercially available and/or are known and/or they can be prepared by known processes (see, for example, Compagnon, Miocque Ann. Chim. (Paris) [14] 5, pp. 11–22, 23–27 (1970)).

The substituted cyclic aminocarboxylic acids of the formula (XVIIIa), in which A and B form a ring are generally obtainable by the Bucherer-Bergs synthesis or by the Strecker synthesis, where they are in each case obtained in different isomeric forms. Thus, the conditions of the Bucherer-Bergs synthesis give mainly the isomers (hereinbelow for the sake of simplicity referred to as β) in which the radicals R and the carboxyl group are in equatorial positions, whereas the conditions of the Strecker synthesis give mainly the isomers (hereinbelow for the sake of simplicity referred to as α) in which the amino group and the radicals R are in equatorial positions.

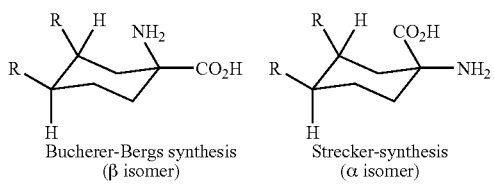

Bucherer-Bergs synthesis (β isomer)    Strecker-synthesis (α isomer)

(L. Munday, J. Chem. Soc. 4372 (1961); J. T. Eward, C. Jitrangeri, Can. J. Chem. 53, 3339(1975).

Furthermore, the starting materials of the formula (II)

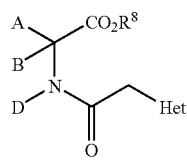

(II)

in which
A, B, D, Het and $R^8$ are each as defined above used in the above process (A) can be prepared by reacting amino nitrites of the formula (XX)

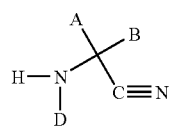

(XX)

in which
A, B and D are each as defined above with substituted hetarylacetic acid derivatives of the formula (XVI)

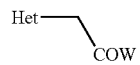

(XVI)

in which
W and Het are each as defined above to give compounds of the formula (XXI)

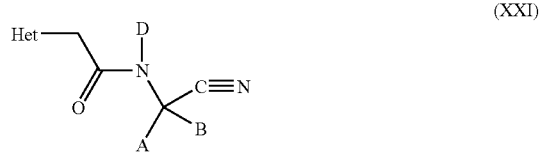

(XXI)

in which
A, B, D and Het are each as defined above which are subsequently subjected to an acidic alcoholysis.

The compounds of the formula (XXI) are likewise novel.

The compounds of the formula (III)

(III)

in which
A, B, Het and $R^8$ are each as defined above required as starting materials in the process (B) according to the invention are novel.

They can be prepared by methods known in principle.

Thus, the compounds of the formula (III) are obtained, for example, when 2-hydroxycarboxylic esters of the formula (XXII)

(XXII)

in which
A, B and $R^8$ are each as defined above are acylated with substituted hetarylacetic acid derivatives of the formula (XVI)

(XVI)

in which
W and Het are each as defined above (Chem. Reviews 52, 237–416 (1953).

Furthermore, compounds of the formula (III) are obtained when substituted hetarylacetic acids of the formula (XIX)

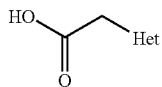 (XIX)

in which

Het is as defined above are alkylated with α-halogenocarboxylic esters of the formula (XXIII)

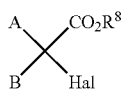 (XXIII)

in which

A, B and $R^8$ are each as defined above and

Hal represents chlorine or bromine.

The compounds of the formula (IV)

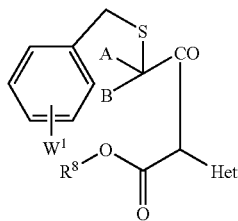 (IV)

in which

A, B, $W^1$, Het and $R^8$ are each as defined above and $W^1$ represents hydrogen, halogen, alkyl (preferably $C_1$–$C_6$-alkyl) or alkoxy (preferably $C_1$–$C_6$-alkoxy)

required as starting materials in the above process (C) are novel.

They can be prepared by methods known in principle.

The compounds of the formula (IV) are obtained, for example, when compounds of the formula (XXIV)

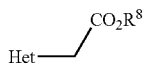 (XXIV)

in which

Het and $R^8$ are each as defined above are acylated with 2-benzylthio-carbonyl halides of the formula (XXV)

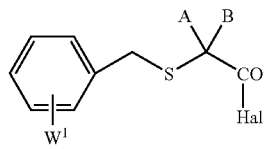 (XXV)

in which

A, B and $W^1$ are each as defined above and

Hal represents halogen (in particular chlorine or bromine)

in the presence of strong bases (see, for example, M. S. Chambers, E. J. Thomas, D. J. Williams, J. Chem. Soc. Chem. Commun., (1987), 1228).

Some of the compounds of the formula (XXIV) are commercially available, some are known, or they can be prepared by known processes:

a) thiazolyl acetic esters: C. S. Rooney et al., J. Med. Chem. 26. 700–714 (1983), EP-A-368 592), M. S. Malmas et al., J. Med. Chem. 39, 237–246 (1996); J. C. Collins et al., J. Med. Chem. 41, 5037–5054 (1998); NL-A-6 614 130.

b) oxazolyl acetic acids: K. Meguro et al., Chem. Pharm. Bull, 34, 2840–2851 (1986), M. Sehi et al., Chem. Pharm. Bull. 36, 4435–4440 (1988), Malmas et al., J. Med. Chem. 39, 237–245 (1996), EP 0 177 353 A2, WO 87/03 807, WO 95/18 125, B. Hulin, J. Med. Chem. 35, 1853–1864 (1992), EP 0 389 699 A 1.

The acyl halides of the formula (V), carboxylic anhydrides of the formula (VI), chloroformic esters or chloroformic thioesters of the formula (VII), chloromonothioformic esters or chlorodithioformic esters of the formula (VIII), sulphonyl chlorides of the formula (IX), phosphorus compounds of the formula (X) and metal hydroxides, metal alkoxides or amines of the formulae (XI) and (XII) and isocyanates of the formula (XIII) and carbamoyl chlorides of the formula (XIV) furthermore required as starting materials for carrying out the processes (D), (E), (F), (G), (H), (I) and (J) according to the invention are generally known compounds of organic or inorganic chemistry.

Some of the compounds of the formulae (XV), (XVIII), (XX), (XXII), (XXIII) and (XXV) are commercially available, some are known, and/or they can be prepared by methods known in principle.

The process (A) is characterized in that compounds of the formula (II) in which A, B, D, Het and $R^8$ are each as defined above are subjected to an intramolecular condensation in the presence of a base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethyl formamide and N-methylpyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)-amine). Alkali metals such as sodium and potassium can also be used. Furthermore, alkali metal and alkaline earth metal halides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperatures can be varied within a relatively wide range. In general, the reaction is carried out at temperatures between −80° C. and 180° C., preferably between −50° C. and 120° C.

The process (A) according to the invention is generally carried out under atmospheric pressure.

When carrying out the process (A) according to the invention, the reaction components of the formula (II) and the deprotonating bases are generally employed in approximately double-equimolar amounts. However, it is also possible to use a relatively large excess (up to 3 mol) of one component or the other.

The process (B) is characterized in that compounds of the formula (III) in which A, B, Het and $R^8$ are each as defined above are subjected to an intramolecular condensation in the presence of a diluent and in the presence of a base.

Suitable diluents for the process (B) according to the invention are all inert organic solvents. Preference is given to using hydrocarbons, such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethyl formamide and N-methylpyrrolidone, and also alcohols, such as methanol, ethanol, propanol, iso-propanol, butanol, iso-butanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperatures can be varied within a relatively wide range. In general, the reaction is carried out at temperatures between −80° C. and 180° C., preferably between −50° C. and 120° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, Het and $R^8$ are each as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methyl-pyrrolidone. Furthermore, it is possible to employ alcohols such as methanol, ethanol, propanol, iso-propanol, butanol, isobutanol, tert-butanol.

If appropriate, the acid used can also serve as diluent.

Suitable acids for the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the reaction is carried out at temperatures between −30° C. and 250° C., preferably between 0° C. and 150° C.

The process (C) according to the invention is generally carried out under atmospheric pressure.

When carrying out the process (C) according to the invention, the reaction components of the formula (IV) and the acid are employed, for example, in equimolar amounts. However, it is also possible, if appropriate, to use the acid as solvent or as catalyst.

The process (D-α) is characterized in that compounds of the formulae (I-1-A-a) to (I-3-B-a) are in each case reacted with carbonyl halides of the formula (V), if appropriate in the presence of a diluent and if appropriate in the presence of an acid binder.

Suitable diluents for the process (D-α) according to the invention are all solvents which are inert towards the acyl halides. Preference is given to using hydrocarbons such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitrites, such as acetonitrile, and also strongly polar solvents, such as dimethylformamide, dimethylacetamide, dimethyl sulphoxide and sulpholane. The hydrolytic stability of the acyl halide permitting, the reaction can also be carried out in the presence of water.

Suitable acid binders for the reaction according to the process (D-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (D-α) according to the invention can be varied within a relatively wide range.

In general, the reaction is carried out at temperatures between −20° C. and +150° C., preferably between 0° C. and 100° C.

When carrying out the process (D-α) according to the invention, the starting materials of the formulae (I-1-A-a) to (I-3-B-a) and the carbonyl halide of the formula (V) are generally in each case employed in approximately equivalent amounts. However, it is also possible to employ a relatively large excess (up to 5 mol) of the carbonyl halide. Work-up is carried out by customary methods.

The process (D-β) is characterized in that compounds of the formulae (I-1-A-a) to (I-3-B-a) are reacted with carboxylic anhydrides of the formula (VI), if appropriate in the presence of a diluent and if appropriate in the presence of an acid binder.

Preferred diluents for the process (D-β) according to the invention are those diluents which are also preferred when acyl halides are used. Otherwise, it is also possible for a carboxylic anhydride employed in excess to act simultaneously as diluent.

In the process (D-β), acid binders which are added, if appropriate, are preferably those acid binders which are also preferred when acyl halides are used.

In the process (D-β) according to the invention, the reaction temperatures can be varied within a relatively wide range. In general, the reaction is carried out at temperatures between −20° C. and +150° C., preferably between 0° C. and 100° C.

When carrying out the process (D-β) according to the invention, the starting materials of the formulae (I-1-A-a) to (I-3-B-a) and the carboxylic anhydride of the formula (VI) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (E) is characterized in that compounds of the formulae (I-1-A-a) to (I-3-B-a) are in each case reacted with chloroformic esters or chloroformic thioesters of the formula (VII), if appropriate in the presence of a diluent and if appropriate in the presence of an acid binder.

Suitable acid binders for the reaction according to process (E) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Suitable diluents for the process (E) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethylacetamide, dimethyl sulphoxide and sulpholane.

When carrying out the process (E) according to the invention, the reaction temperatures can be varied within a relatively wide range. If the reaction is carried out in the presence of a diluent and an acid binder, the reaction temperatures are generally between −20° C. and +100° C., preferably between 0° C. and 50° C.

The process (E) according to the invention is generally carried out under atmospheric pressure.

When carrying out the process (E) according to the invention, the starting materials of the formulae (I-1-A-a) to (I-3-B-a) and the appropriate chloroformic ester or chloroformic thioester of the formula (VII) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping the diluent.

The process (F) according to the invention is characterized in that compounds of the formulae (I-1-A-a) to (I-3-B-a) are in each case reacted with compounds of the formula (VIII) in the presence of a diluent and, if appropriate, in the presence of an acid binder.

In the preparation process (F), approximately 1 mole of chloromonothioformic ester or chlorodithioformic ester of the formula (VIII) is reacted per mole of starting material of the formulae (I-1-A-a) to (I-3-B-a), at from 0 to 120° C., preferably from 20 to 60° C.

Suitable diluents which are added, if appropriate, are all inert polar organic solvents, such as nitrites, esters, ethers, amides, sulphones, sulphoxides, but also halogenoalkanes.

Preference is given to using acetonitrile, ethyl acetate, dimethylsulphoxide, tetrahydrofuran, dimethylformamide or methylene chloride.

If, in a preferred embodiment, the enolate salt of the compounds (I-1-A-a) to (I-3-B-a) is prepared by addition of strong deprotonating agents, such as, for example, sodium hydride or potassium tert-butoxide, it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (G) according to the invention is characterized in that compounds of the formulae (I-1-A-a) to (I-3-B-a) are in each case reacted with sulphonyl chlorides of the formula (IX), if appropriate in the presence of a diluent and if appropriate in the presence of an acid binder.

In the preparation process (G), approximately 1 mole of sulphonyl chloride of the formula (IX) is reacted per mole of starting material of the formulae (I-1-A-a) to (I-3-B-a) at from −20 to 150° C., preferably at from 20 to 70° C.

Suitable diluents which are added if appropriate are all inert polar organic solvents, such as nitrites, esters, ethers, amides, sulphones, sulphoxides or halogenated hydrocarbons, such as methylene chloride.

Preference is given to using acetonitrile, ethyl acetate, dimethyl sulphoxide, tetrahydrofuran, dimethylformamide, methylene chloride.

If, in a preferred embodiment, the enolate salt of the compounds (I-1-A-a) to (I-3-B-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (H) according to the invention is characterized in that compounds of the formulae (I-1-A-a) to (I-3-B-a) are in each case reacted with phosphorus compounds of the formula (X), if appropriate in the presence of a diluent and if appropriate in the presence of an acid binder.

In the preparation process (H), 1 to 2, preferably 1 to 1.3, mol of the phosphorus compound of the formula (X) are reacted per mole of the compounds (I-1-A-a) to (I-3-B-a), at temperatures between −40° C. and 150° C., preferably between −10 and 110° C., to give compounds of the formulae (I-1-A-e) to (I-3-B-e).

Suitable solvents which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Examples include sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (I) is characterized in that compounds of the formulae (I-1-A-a) to (I-3-B-a) are reacted with metal hydroxides or metal alkoxides of the formula (XI) or amines of the formula (XII), if appropriate in the presence of a diluent.

Preferred diluents for the process (I) according to the invention are ethers, such as tetrahydrofuran, dioxane, diethyl ether, or else alcohols, such as methanol, ethanol, isopropanol, but also water.

The process (I) according to the invention is generally carried out under atmospheric pressure.

The reaction temperatures are generally between −20° C. and 100° C., preferably between 0° C. and 50° C.

The process (J) according to the invention is characterized in that compounds of the formulae (I-1-A-a) to (I-3-B-a) are in each case reacted (J-α) with compounds of the formula (XIII), if appropriate in the presence of a diluent and if appropriate in the presence of a catalyst, or (J-β) with compounds of the formula (XIV), if appropriate in the presence of a diluent and if appropriate in the presence of an acid binder.

In the preparation process (J-α), approximately 1 mole of isocyanate of the formula (XIII) is reacted per mole of starting material of the formulae (I-1-A-a) to (I-3-B-a), at from 0 to 100° C., preferably at from 20 to 50° C.

Suitable diluents which are added, if appropriate, are all inert organic solvents, such as ethers, amides, nitrites, sulphones, sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In the preparation process (J-β), approximately 1 mole of carbamoyl chloride of the formula (XIV) is reacted per mole of starting material of the formulae (I-1-A-a) to (I-3-B-a), at from −20 to 150° C., preferably from 0 to 70° C.z Suitable diluents which are added, if appropriate, are all inert polar organic solvents, such as nitrites, esters, ethers, amides, sulphones, sulphoxides or halogenated hydrocarbons.

Preference is given to using acetonitrile, ethyl acetate, dimethyl sulphoxide, tetrahydrofuran, dimethylformamide or methylene chloride.

If, in a preferred embodiment, the enolate salt of the compounds (I-1-A-a) to (I-3-B-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis*, *Thrips tabaci*, *Thrips palmi* and *Frankliniella accidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp., *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon soistitialis*, *Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp., *Brevipalpus* spp.

The phytoparasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetical engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I). The preferred ranges stated above for the active compounds also apply to the treatment of these plants. Particular emphasis is given to the treatment of plants with the mixtures specifically mentioned in the present text.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl{2-methyl-1-[[[1-(4-methylphenyl)ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate, methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, Verticillium lecanii,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate.
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid;
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp.,*Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa spp*.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical sorvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile *Oligochaeta,* such as *Serpulidae,* and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

Algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

Fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

Molluscicides such as
fentin acetate, metaldehyde, methiocarb, niclosamid, thiodicarb and trimethacarb; or conventional antifouling active compounds such as
4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetramethylthiuram disulfide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds; small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example I-1-A-a-1

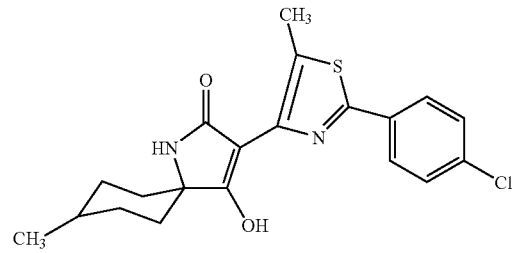

At 0° C., 3.70 g (0.031 mol) of potassium tert-butoxide are initially charged in 26 ml of anhydrous DMF, and 6 g of the compound according to Example II-1 in 12 ml of anhydrous DMF are added. The mixture is stirred at 20° C. for 1 h.

The reaction solution is added to 200 ml of ice-water and acidified at 0–10° C. The precipitate is then filtered off with suction and recrystallized.

Yield: 4.66 g, ( ≙83% of theory), m.p. >260° C.

DMF (dimethylformamide)

The following compounds of the formula (I-1-A-a) are obtained similarly to Example (I-1-A-a-1) and in accordance with the general statements on the preparation (I-1-A-a)

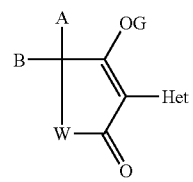

| Ex. No. | X | Y | D | A | B | m.p.° C. | isomer |
|---|---|---|---|---|---|---|---|
| I-1-A-a-2 | —CH$_3$ | 4-Cl—C$_6$H$_4$ | H | CH$_3$ | CH$_3$ | 230 | — |
| I-1-A-a-3 | —CH$_3$ | 4-Cl—C$_6$H$_4$ | H | —(CH$_2$)$_2$—CHOCH$_3$—(CH$_2$)$_2$— | | 246 | β |
| I-1-A-a-4 | —CH$_3$ | 4-Cl—C$_6$H$_5$ | H | —(CH$_2$)$_2$—CHOC$_2$H$_5$—(CH$_2$)$_2$— | | >250 | β |
| I-1-A-a-5 | —CH$_3$ | 4-Cl—C$_6$H$_4$ | H | —(CH$_2$)$_2$O—(CH$_2$)$_2$— | | >265 | — |
| I-1-A-a-6 | —CH$_3$ | 4-Cl—C$_6$H$_4$ | H | —CH$_2$—O—(CH$_2$)$_3$— | | >250 | — |
| I-1-A-a-7 | —C$_2$H$_5$ | 4-Cl—C$_6$H$_4$ | H | —(CH$_2$)$_2$—CHOCH$_3$—(CH$_2$)$_2$— | | 250 | β |
| I-1-A-a-8 | —CH$_3$ | 4-CH$_3$—C$_6$H$_4$ | H | —(CH$_2$)$_2$—CHOCH$_3$—(CH$_2$)$_2$— | | 244 | β |
| I-1-A-a-9 | —CH$_3$ | CH$_3$ | H | —(CH$_2$)$_2$—CHOCH$_3$—(CH$_2$)$_2$— | | 406 | β |
| I-1-A-a-10 | —C$_2$H$_5$ | 4-Cl—C$_6$H$_4$ | H | CH$_3$ | CH$_3$ | 176 | — |
| I-1-A-a-11 | —CH$_3$ | C$_6$H$_5$ | H | —(CH$_2$)$_2$—CHOCH$_3$—(CH$_2$)$_2$— | | 235 | β |
| I-1-A-a-12 | —CH$_3$ | 2-Cl, 6-OCH$_3$—C$_6$H$_3$ | H | —(CH$_2$)$_2$—CHOCH$_3$—(CH$_2$)$_2$— | | 249 | β |
| I-1-A-a-13 | —CH$_3$ | 4-CH$_3$—C$_6$H$_4$ | H | CH$_3$ | CH$_3$ | 228 | — |
| I-1-A-a-14 | —CH$_3$ | C$_6$H$_5$ | H | CH$_3$ | CH$_3$ | 177 | — |
| I-1-A-a-15 | —C$_3$H$_7$ | 4-Cl—C$_6$H$_4$ | H | —(CH$_2$)$_2$—CHOCH$_3$—(CH$_2$)$_2$— | | 204 | β |
| I-1-A-a-16 | —CH$_3$ | 2-Cl—C$_6$H$_4$ | H | —(CH$_2$)$_2$—CHOCH$_3$—(CH$_2$)$_2$— | | 235 | β |
| I-1-A-a-17 | —CH$_3$ | 2,4-Cl$_2$—C$_6$H$_3$ | H | —(CH$_2$)$_2$—CHOCH$_3$—(CH$_2$)$_2$— | | 235 | β |
| I-1-A-a-18 | —CH$_3$ | 4-CF$_3$—C$_6$H$_4$ | H | —(CH$_2$)$_2$—CHOCH$_3$—(CH$_2$)$_2$— | | 258 | β |
| I-1-A-a-19 | —CH$_3$ | 3-CF$_3$—C$_6$H$_4$ | H | CH$_3$ | CH$_3$ | 172 | — |
| I-1-A-a-20 | —CH$_3$ | 2,4-Cl$_2$—C$_6$H$_3$ | H | CH$_3$ | CH$_3$ | 211 | — |
| I-1-A-a-21 | —CH$_3$ | 4-CF$_3$—C$_6$H$_4$ | H | CH$_3$ | CH$_3$ | 220 | — |
| I-1-A-a-22 | —CH$_3$ | 2-Cl—C$_6$H$_4$ | H | CH$_3$ | CH$_3$ | 218 | — |
| I-1-A-a-23 | —C$_3$H$_7$ | 4-Cl—C$_6$H$_4$ | H | CH$_3$ | CH$_3$ | | — |
| I-1-A-a-24 | Br | 4-Cl—C$_6$H$_4$ | H | —(CH$_2$)$_2$—CHOCH$_3$—(CH$_2$)$_2$— | | | β |

-continued

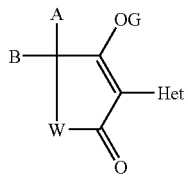

(I-1-A-a)

| Ex. No. | X | Y | D | A | B | m.p.° C. | isomer |
|---|---|---|---|---|---|---|---|
| I-1-A-a-25 | CH₃ | 4-F₃C-C₆H₄-C₆H₄- | H | —(CH₂)₂—CHOCH₃—(CH₂)₂— | | | β |
| I-1-A-a-26 | Cl | 4-Cl—C₆H₄ | H | —(CH₂)₂—CHOCH₃—(CH₂)₂— | | | β |
| I-1-A-a-27 | Br | 4-Cl—C₆H₄ | H | CH₃ | CH₃ | 143 | — |
| I-1-A-a-28 | Cl | 4-Cl—C₆H₄ | H | CH₃ | CH₃ | 208 | — |
| I-1-A-a-29 | CH₃ | 4-F₃C-C₆H₄-C₆H₄- | H | CH₃ | CH₃ | 226 | — |
| I-1-A-a-30 | CH₃ | 4-Cl—C₆H₄— | H | —CH—(CH₂)₂—CH—CH₂—  with —CH₂— bridge | | | β |
| I-1-A-a-31 | C₃H₇ | 4-Cl—C₆H₄ | H | CH₃ | CH₃ | 162 | — |
| I-1-A-a-32 | CH₃ | 2-Cl—C₆H₄ | H | —(CH₂)₂—CHOCH₃—(CH₂)₂— | | 261 | α |
| I-1-A-a-33 | CH₃ | 3-Cl—C₆H₄ | H | —(CH₂)₂—CHOCH₃—(CH₂)₂— | | 245 | β |
| I-1-A-a-34 | CH₃ | 3-Cl—C₆H₄ | H | CH₃ | CH₃ | 212 | — |
| I-1-A-a-35 | CH₃ | 4-Cl—C₆H₄—CH₂— | H | CH₃ | CH₃ | 139 | — |
| I-1-A-a-36 | CH₃ | 4-CF₃—C₆H₄ | H | —(CH₂)₂—CHOCH₃—(CH₂)₂— | | 220 | α |
| I-1-A-a-37 | CH₃ | 4-Cl—C₆H₄—CH₂— | H | —(CH₂)₂—CHOCH₃—(CH₂)₂— | | 205 | β |
| I-1-A-a-38 | i-C₃H₇ | 4-Cl—C₆H₄ | H | —(CH₂)₂—CHOCH₃—(CH₂)₂— | | 274 | β |
| I-1-A-a-39 | CH₃ | C₆H₅—O—C₆H₄— | H | CH₃ | CH₃ | 181 | — |
| I-1-A-a-40 | CH₃ | 2,2-difluoro-5-methylbenzo[1,3]dioxole | H | CH₃ | CH₃ | 205 | — |
| I-1-A-a-41 | CH₃ | biphenyl | H | CH₃ | CH₃ | 254 | — |
| I-1-A-a-42 | CH₃ | C₆H₅—O—C₆H₄— | H | —(CH₂)₂—CHOCH₃—(CH₂)₂— | | 225 | β |
| I-1-A-a-43 | CH₃ | 4-(CH₃)₃C—C₆H₄ | H | —(CH₂)₂—CHOCH₃—(CH₂)₂— | | 252 | β |
| I-1-A-a-44 | CH₃ | 4-Cl—C₆H₄ | H | —(CH₂)₂—C(CH₃)₂—(CH₂)₂— | | 291 | — |
| I-1-A-a-45 | CH₃ | 4-Cl—C₆H₄ | —(CH₂)₂—S—CH₂— | | H | 197 | — |
| I-1-A-a-46 | CH₃ | C₆H₅—O—C₆H₄— | H | —(CH₂)₂—CHOCH₃—(CH₂)₂— | | 252 | α |
| I-1-A-a-47 | CH₃ | 5-methylbenzo[1,3]dioxole | H | CH₃ | CH₃ | 121 | — |
| I-1-A-a-48 | CH₃ | 4-Cl—C₆H₄ | —(CH₂)₄— | | H | | |

Example I-1-A-b-1

Example I-1-A-c-1

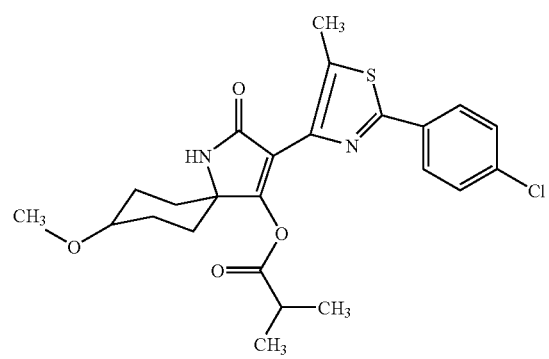

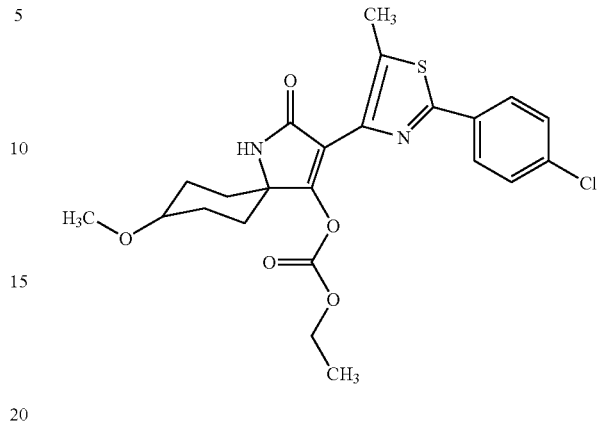

0.81 g of the compound according to Example I-1-a-2 is initially charged in 10 ml of anhydrous ethyl acetate and heated at reflux with 0.3 ml (2.2 mmol) of triethylamine. 0.25 ml (0.0022 mol) of isobutyryl chloride in 5 ml of anhydrous ethyl acetate is then added, and the mixture is heated at reflux.

After the reaction has ended (TLC), the solvent is distilled off and the residue is taken up in dichloromethane, washed twice with 10 ml of 0.5 N NaOH, dried and concentrated using a rotary evaporator. The residue is purified by silica gel column chromatography (dichloromethane/ethyl acetate, 3:1).

Yield: 0.2 g ( ≙21% of theory) m.p. 208° C.

The following compounds of the formula (I-1-A-b) are obtained similarly to Example (I-1-A-b-1) and in accordance with the general statements on the preparation 0.69 g of the compound according to Example I-1-a-2 is initially charged in 10 ml of anhydrous dichloromethane and, at 10° C., admixed with 0.24 ml (1.7 mmol) of triethylamine.

0.17 ml (1.7 mmol) of ethyl chloroformate in 1 ml of anhydrous dichloromethane is then added, and the mixture is stirred at room temperature.

After the reaction has ended (TLC), the solvent is distilled off and the residue is taken up in dichloromethane, washed twice with 10 ml of 0.5 N NaOH, dried and concentrated using a rotary evaporator. The residue is purified by silica gel column chromatography (dichloromethane/ethyl acetate, 3:1).

Yield: 0.58 g ( ≙71% of theory), m.p. 211° C.

The following compounds of the formula (I-1-A-c) are obtained similarly to Example (I-1-A-c-1) and in accordance with the general statements on the preparation (I-1-A-b)

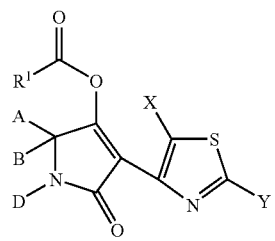

| Ex. No | X | Y | D | A | B | $R^1$ | m.p.° C. | isomer |
|---|---|---|---|---|---|---|---|---|
| I-1-A-b-2 | $CH_3$ | 4-Cl—$C_6H_4$ | H | —$(CH_2)_2$—CHOCH$_3$—$(CH_2)_2$— | | Cl—C$_6$H$_4$— | 273 | — |
| I-1-A-b-3 | $CH_3$ | 4-Cl—$C_6H_4$ | H | —$(CH_2)_2$—CHOCH$_3$—$(CH_2)_2$— | | Cl—pyridyl— | 249 | β |

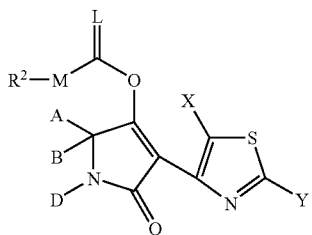

(I-1-A-c)

| Ex. No. | X | Y | D | A | B | L | M | R² | m.p.° C. | isomer |
|---|---|---|---|---|---|---|---|---|---|---|
| I-1-A-c-2 | $CH_3$ | 4-Cl—$C_6H_4$ | H | —$(CH_2)_2$—$CHOCH_3$—$(CH_2)_2$— | | O | O | $C_6H_5$ | — | β |
| I-1-A-c-3 | $CH_3$ | 4-Cl—$C_6H_4$ | H | —$(CH_2)_2$—$CHOCH_3$—$(CH_2)_2$— | | O | O | $C_6H_5$—$CH_2$— | 292 | β |
| I-1-A-c-4 | $CH_3$ | $CH_3$ | H | —$(CH_2)_2$—$CHOCH_3$—$(CH_2)_2$— | | O | O | $C_2H_5$ | — | β |

Example II-A-1

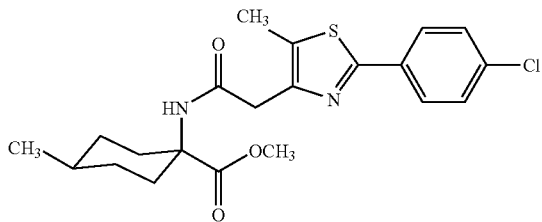

6.6 ml of triethylamine are added to 4.61 g of methyl 4-methyl-1-amino-cyclohexane-1-carboxylate hydrochloride in 80 ml of anhydrous tetrahydrofuran, and the mixture is stirred for 3 min. 5.3 g of 4-[2-(4-chlorophenyl)-5-methyl]-thiazolyl-acetic acid are added. The mixture is stirred at room temperature for another 15 min. 4.4 ml of triethylamine are then added, followed immediately by dropwise addition of 1.12 ml of phosphorus oxychloride such that the solution boils moderately. The solution is heated at reflux for 30 min.

The reaction solution is poured into 200 ml of ice-water, extracted with dichloromethane and dried. The solvent is distilled off and the residue is recrystallized.

Yield: 6.19 g ( ≙73% of theory), m.p.: 150° C.

The following compounds of the formula (II-A) are obtained similarly to Examples (II-A-1) and (II-A-48) and in accordance with the general statements on the preparation

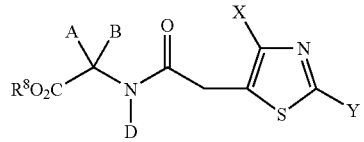

(II-A)

| Ex. No. | X | Y | D | A | B | R⁸ | m.p.° C. | isomer |
|---|---|---|---|---|---|---|---|---|
| II-A-2 | $CH_3$ | 4-Cl—$C_6H_4$ | H | —$(CH_2)_2$—$CHOCH_3$—$(CH_2)_2$— | | $CH_3$ | 121 | β |
| II-A-3 | $CH_3$ | 4-Cl—$C_6H_4$ | H | —$(CH_2)_2$—$CHOC_2H_5$—$(CH_2)_2$— | | $CH_3$ | 120 | β |
| II-A-4 | $CH_3$ | 4-Cl—$C_6H_4$ | H | —$(CH_2)_2$—O—$(CH_2)_2$— | | $CH_3$ | 201 | — |
| II-A-5 | $CH_3$ | 4-Cl—$C_6H_4$ | H | —$CH_2$—O—$(CH_2)_3$— | | $CH_3$ | 132 | — |
| II-A-6 | $CH_3$ | 4-Cl—$C_6H_4$ | H | $CH_3$ | $CH_3$ | $CH_3$ | 139 | — |
| II-A-7 | $C_2H_5$ | 4-Cl—$C_6H_4$ | H | —$(CH_2)_2$—$CHOCH_3$—$(CH_2)_2$— | | $CH_3$ | 124 | β |
| II-A-8 | $C_2H_5$ | 4-Cl—$C_6H_4$ | H | $CH_3$ | $CH_3$ | $CH_3$ | 106 | — |
| II-A-9 | $C_2H_5$ | 4-$CH_3$—$C_6H_4$ | H | $CH_3$ | $CH_3$ | $CH_3$ | 164 | — |
| II-A-10 | $CH_3$ | $C_6H_5$ | H | $CH_3$ | $CH_3$ | $CH_3$ | 142 | — |
| II-A-11 | $CH_3$ | 4-$CH_3$—$C_6H_4$ | H | —$(CH_2)_2$—$CHOCH_3$—$(CH_2)_2$— | | $CH_3$ | 119 | β |
| II-A-12 | $CH_3$ | $C_6H_5$ | H | —$(CH_2)_2$—$CHOCH_3$—$(CH_2)_2$— | | $CH_3$ | 143 | β |
| II-A-13 | $CH_3$ | $CH_3$ | H | —$(CH_2)_2$—$CHOCH_3$—$(CH_2)_2$— | | $CH_3$ | Öl | β |
| II-A-14 | $CH_3$ | 2-Cl, 6-F—$C_6H_3$ | H | —$(CH_2)_2$—$CHOCH_3$—$(CH_2)_2$— | | $CH_3$ | Öl | β |
| II-A-15 | $C_3H_7$ | 4-Cl—$C_6H_4$ | H | —$(CH_2)_2$—$CHOCH_3$—$(CH_2)_2$— | | $CH_3$ | 114 | β |

-continued (II-A)

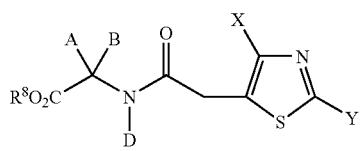

| Ex. No. | X | Y | D | A | B | R⁸ | m.p.° C. | isomer |
|---|---|---|---|---|---|---|---|---|
| II-A-16 | CH₃ | 2-Cl—C₆H₄ | H | —(CH₂)₂—CHOCH₃—(CH₂)₂— | | CH₃ | 128 | β |
| II-A-17 | C₃H₇ | 4-Cl—C₆H₄ | H | CH₃ | CH₃ | CH₃ | 129 | — |
| II-A-18 | CH₃ | 2-Cl—C₆H₄ | H | CH₃ | CH₃ | CH₃ | 112 | — |
| II-A-19 | CH₃ | 2,4-Cl₂—C₆H₃ | H | CH₃ | CH₃ | CH₃ | 136 | — |
| II-A-20 | CH₃ | 4-CF₃—C₆H₄ | H | CH₃ | CH₃ | CH₃ | 119 | — |
| II-A-21 | CH₃ | 2,4-Cl₂—C₆H₃ | H | —(CH₂)₂—CHOCH₃—(CH₂)₂— | | CH₃ | 124 | β |
| II-A-22 | CH₃ | 4-CF₃—C₆H₄ | H | —(CH₂)₂—CHOCH₃—(CH₂)₂— | | CH₃ | 110 | β |
| II-A-23 | CH₃ | 3-Cl—C₆H₄ | H | —(CH₂)₂—CHOCH₃—(CH₂)₂— | | CH₃ | 130 | β |
| II-A-24 | CH₃ | 3-Cl—C₆H₄ | H | CH₃ | CH₃ | CH₃ | 135 | — |
| II-A-25 | CH₃ | 3-CF₃—C₆H₄ | H | CH₃ | CH₃ | CH₃ | 160 | — |
| II-A-26 | Cl | 4-Cl—C₆H₄ | H | —(CH₂)₂—CHOCH₃—(CH₂)₂— | | CH₃ | 129 | β |
| II-A-27 | CH₃ | F₃C—⟨C₆H₄⟩—⟨C₆H₄⟩— | H | —(CH₂)₂—CHOCH₃—(CH₂)₂— | | CH₃ | 168 | β |
| II-A-28 | Br | 4-Cl—C₆H₄ | H | CH₃ | CH₃ | CH₃ | 127 | — |
| II-A-29 | CH₃ | 3,4-Cl₂—C₆H₃ | H | CH₃ | CH₃ | CH₃ | 163 | — |
| II-A-30 | CH₃ | F₃C—⟨C₆H₄⟩—⟨C₆H₄⟩— | H | CH₃ | CH₃ | CH₃ | 160 | — |
| II-A-31 | Cl | 4-Cl—C₆H₄ | H | CH₃ | CH₃ | CH₃ | 144 | — |
| II-A-32 | i-C₃H₇ | 4-Cl—C₆H₄ | H | —(CH₂)₂—CHOCH₃—(CH₂)₂— | | CH₃ | 123 | β |
| II-A-33 | CH₃ | 4-Cl—C₆H₄—CH₂ | H | —(CH₂)₂—CHOCH₃—(CH₂)₂— | | CH₃ | 108 | β |
| II-A-34 | CH₃ | 4-Cl—C₆H₄—CH₂ | H | CH₃ | CH₃ | CH₃ | 109 | — |
| II-A-35 | CH₃ | ⟨C₆H₅⟩—O—⟨C₆H₄⟩— | H | —(CH₂)₂—CHOCH₃—(CH₂)₂— | | CH₃ | 108 | β |
| II-A-36 | CH₃ | benzo[1,3]dioxole-yl | H | CH₃ | CH₃ | CH₃ | 132 | — |
| II-A-37 | CH₃ | ⟨C₆H₅⟩—O—⟨C₆H₄⟩— | H | CH₃ | CH₃ | CH₃ | Öl | — |
| II-A-38 | CH₃ | benzo[1,3]dioxole-yl | H | —(CH₂)₂—CHOCH₃—(CH₂)₂— | | CH₃ | 118 | β |
| II-A-39 | CH₃ | 4-Cl—C₆H₄ | H | —(CH₂)₂—C(CH₃)₂—(CH₂)₂— | | CH₃ | 177 | — |
| II-A-40 | CH₃ | 2,2-difluoro-benzo[1,3]dioxole-yl | H | —(CH₂)₂—CHOCH₃—(CH₂)₂— | | CH₃ | 157 | β |
| II-A-41 | CH₃ | biphenyl-yl | H | —(CH₂)₂—CHOCH₃—(CH₂)₂— | | CH₃ | 137 | β |
| II-A-42 | CH₃ | 4-(CH₃)₃C—C₆H₄ | H | —(CH₂)₂—CHOCH₃—(CH₂)₂— | | CH₃ | 115 | β |

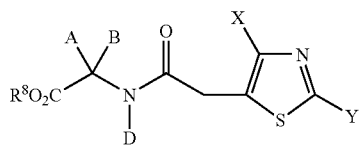

(II-A)

| Ex. No. | X | Y | D | A | B | R⁸ | m.p.° C. | isomer |
|---|---|---|---|---|---|---|---|---|
| II-A-43 | $CH_3$ | (2,2-difluoro-benzodioxol-5-yl) | H | $CH_3$ | $CH_3$ | $CH_3$ | 125 | — |
| II-A-44 | $CH_3$ | (biphenyl-4-yl) | H | $CH_3$ | $CH_3$ | $CH_3$ | 146 | — |
| II-A-45 | $CH_3$ | $4\text{-Cl}-C_6H_4$ | $-(CH_2)_4-$ | | H | $C_2H_5$ | Öl | — |
| II-A-46 | $CH_3$ | $4\text{-Cl}-C_6H_4$ | $-(CH_2)_2-S-CH_2-$ | | H | $C_2H_5$ | Öl | — |
| II-A-47 | $CH_3$ | $4\text{-Cl}-C_6H_4$ | $i\text{-}C_3H_7$ | H | H | $C_2H_5$ | Öl | — |
| II-A-48 | $CH_3$ | $4\text{-Cl}-C_6H_4$ | H | cyclopropyl | $CH_3$ | $CH_3$ | | |
| II-A-49 | $CH_3$ | $4\text{-Cl}-C_6H_4$ | H | $i\text{-}C_3H_7$ | $CH_3$ | $CH_3$ | | |
| II-A-50 | $CH_3$ | $4\text{-Cl}-C_6H_4$ | H | $-CH-(CH_2)_2-CH-CH_2-$ with $-CH_2-$ bridge | | $CH_3$ | | β |
| II-A-51 | $CH_3$ | $4\text{-Cl}-C_6H_4$ | H | $-CH-(CH_2)_2-CH-CH_2-$ with $-CH_2-$ bridge | | $CH_3$ | | α |
| II-A-52 | Br | $4\text{-Cl}-C_6H_4$ | H | $-(CH_2)_2-CHOCH_3-(CH_2)_2-$ | | $CH_3$ | 127 | β |
| II-A-53 | $CH_3$ | $3,4\text{-Cl}_2-C_6H_3$ | H | $-(CH_2)_2-CHOCH_3-(CH_2)_2-$ | | $CH_3$ | | β |
| II-A-54 | $CH_3$ | $4\text{-Br}-C_6H_4$ | H | $-(CH_2)_2-CHOCH_3-(CH_2)_2-$ | | $CH_3$ | 136 | β |

Example No. II-A-48

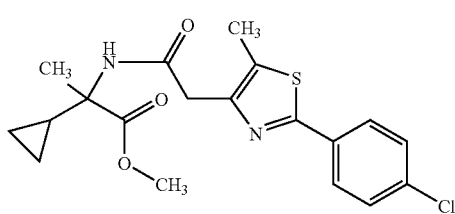

7.4 g (0.075 mol) of concentrated sulphuric acid are initially charged, and 5.37 g of the compound according to Preparation Example XXI-A-1 in 30 ml of methylene chloride are then added dropwise at an internal temperature of from 30 to 40° C. The mixture is then stirred at from 30 to 40° C. for 2 hours. 11 ml of absolute methanol are added dropwise such that an internal temperature of 40° C. results. Stirring is continued at from 40 to 70° C. for 6 hours.

The reaction solution is poured onto 0.08 kg of ice. The mixture is extracted with dichloromethane, the extract is washed with $NaHCO_3$ solution and dried and the solvent is distilled off. The residue is then purified by silica gel column chromatography (dichloromethane/ethyl acetate, 5:1).

This gives 0.42 g ( ≙7% of theory), m.p. 131° C.

Example XXI-A-1

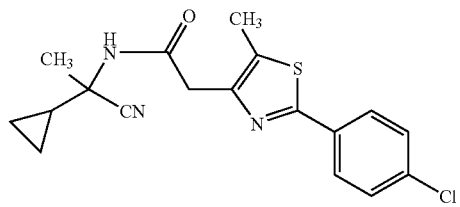

3.7 g of 2-amino-2-cyclopropyl-propionitrile in 60 ml of absolute tetrahydrofuran and 4.92 ml of triethylamine are stirred for 5 min. 8.03 g of 5-methyl-2-(4-chloro-phenyl)-thiazolylacetic acid are then added, and the mixture is stirred at room temperature for 15 min. 6.6 ml of triethylamine are added, followed immediately by dropwise addition of 1.68 ml of phosphorus oxychloride such that the solution boils moderately.

The solution is stirred at reflux for 30 min. The solvent is then distilled off and the residue is purified by silica gel column chromatography (n-hexane/ethyl acetate, 2:1).

Yield: 5.37 g (49% of theory), m.p. 114° C.

The following compounds of the formula (XXI-A) are obtained similarly to Example (XXI-A-1) and in accordance with the general statements on the preparation

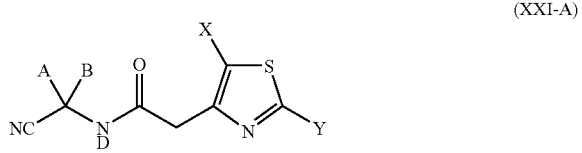

(XXI-A)

| Ex. No. | X | Y | D | A | B | m.p.° C. |
|---|---|---|---|---|---|---|
| XXI-1-A-2 | $CH_3$ | 4-Cl—$C_6H_4$ | H | —$(CH_2)_2$—$C(CH_3)_2$—$(CH_2)_2$— | | 147 |
| XXI-1-A-3 | $CH_3$ | 4-Cl—$C_6H_4$ | H | i-$C_3H_7$ | $CH_3$ | 134 |
| XXI-1-A-4 | $CH_3$ | 4-Cl—$C_6H_4$ | H | —CH—$(CH_2)_2$—CH—$CH_2$— (—$CH_2$—) | | 151 |

Example I-2-A-a-1

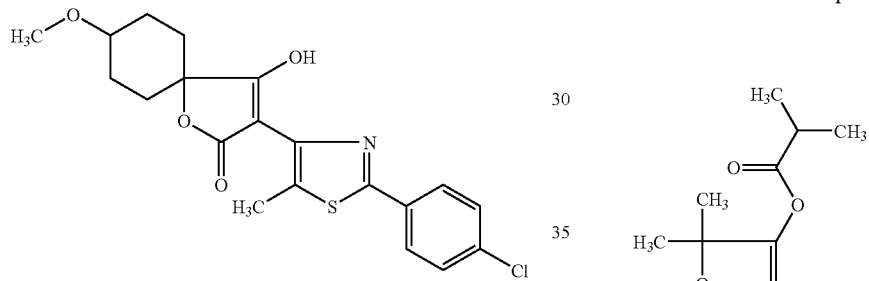

With ice-cooling, 6.6 ml of 1 M potassium tert-butoxide solution are added to 2.48 g (5.49 mmol) of the compound according to Example III-1 in 10 ml of anhydrous DMF, and the mixture is stirred at room temperature overnight. The solvent is distilled off and the residue is dissolved in water, acidified slowly with conc. HCl, filtered off with suction and dried. Yield: 2 g ( ≙89% of theory), m.p. 117–120° C.

The following compounds of the formula (I-2-A-a) are obtained similarly to Example (I-2-A-a-1) and in accordance with the general statements on the preparation Ex. No. I-2-A-a-3 δ=1.45–2.25 (m, 8H), 2.90/3.00 (2s, 3H), 3.30/3.40 (2s, 3H), 3.25/3.50 (2m, 1H), 7.35–8.25 (m, 5H).

Ex. No. I-2-A-a-4 δ=1.60 (s, 6H), 2.95 (s, 3H), 7.45 (m, 3H), 7.80 (m, 2H).

Example I-2-A-b-1

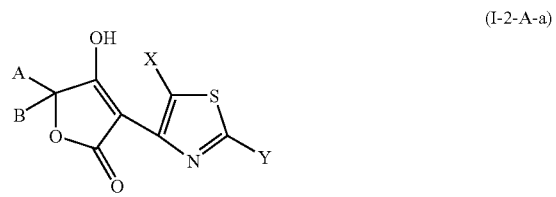

At from 0 to 10° C., 0.244 g (2.3 mmol) of isobutyryl chloride is added to 0.7 g (2.1 mmol) of the compound according to Preparation Example III-A-2 in absolute dichloromethane and 0.232 g (2.3 mmol) of triethylamine, (I-2-A-a)

| Ex. No. | X | Y | A | B | m.p.° C. |
|---|---|---|---|---|---|
| I-2-A-a-2 | $CH_3$ | 4-Cl—$C_6H_4$ | $CH_3$ | $CH_3$ | 133–135 |
| I-2-A-a-3 | $CH_3$ | $C_6H_5$ | —$(CH_2)_2$—$CHOCH_3$—$(CH_2)_2$— | | |
| I-2-A-a-4 | $CH_3$ | $C_6H_5$ | $CH_3$ | $CH_3$ | |

$^1$H-NMR(CDCl$_3$)

and the mixture is stirred at room temperature for 8 hours. The reaction solution is washed with 10% citric acid and 10% NaOH solution. The organic phase is separated off, dried and concentrated.

The residue is purified by silica gel column chromatography (dichloromethane/ethyl acetate, 20/1).

Yield: 0.1 g ≙11.8% of theory, m.p. 95–98° C.

Example I-2-A-c-1

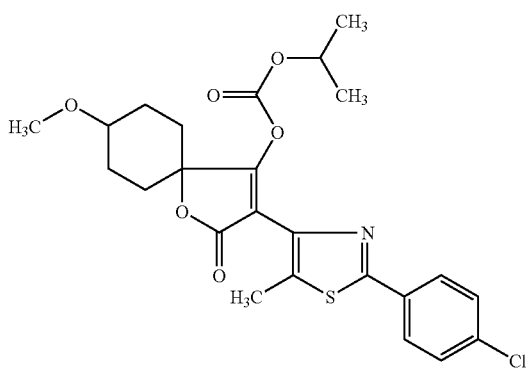

At from 0 to 10° C., isopropyl chloroformate (0.249 g, 2 mmol, 1 M in toluene) is added to 0.75 g (1.85 mmol) of Example I-2-A-1 in absolute dichloromethane and 0.206 g (2 mmol) of triethylamine. The mixture is stirred at room temperature for 8 hours and then washed with 10% citric acid solution and with 10% strength NaOH solution. The organic phase is separated off and dried, and the solvent is removed by distillation.

The residue is purified by silica gel column chromatography (dichloromethane/ethyl acetate, 20/1).

Yield: 0.37 g ≙40% of theory, m.p. 140–145° C.

Example III-A-1

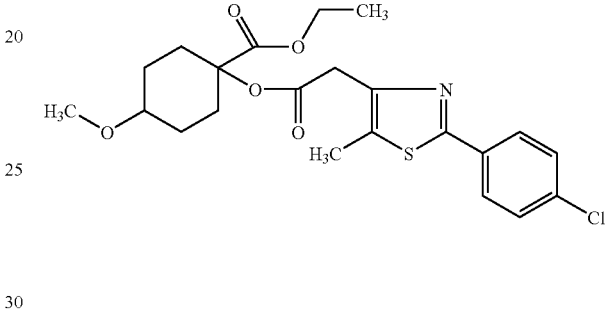

1.11 g (5.49 mmol) of ethyl 4-methoxy-1-hydroxy-cyclohexane-1-carboxylate and 1.57 g (5.49 mmol) of the compound according to Example XVI-1 are stirred at 140° C. for 6 h, the mixture is cooled and the HCl gas is flushed out using argon.

Yield: 2.4 g ( ≙41.62% of theory), logP (acidic) 4.54 (HPLC; acetonitrile).

The following compounds of the formula (III-A) are prepared analogously to Example (III-A-1) and in accordance with the general statements on the preparation

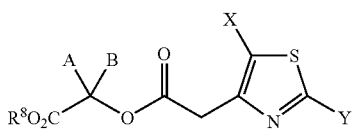
(III-A)

| Ex. No. | X | Y | A | B | R$^8$ | m.p.° C. |
|---|---|---|---|---|---|---|
| III-A-2 | CH$_3$ | 4-Cl—C$_6$H$_4$ | CH$_3$ | CH$_3$ | C$_2$H$_5$ | logP$_{(pH2)}$ 4.53 |
| III-A-3 | CH$_3$ | C$_6$H$_5$ | —(CH$_2$)$_2$—CHOCH$_3$—(CH$_2$)$_2$— | | C$_2$H$_5$ | |
| III-A-4 | CH$_3$ | C$_6$H$_5$ | CH$_3$ | CH$_3$ | C$_2$H$_5$ | |

Example I-3-A-a-1

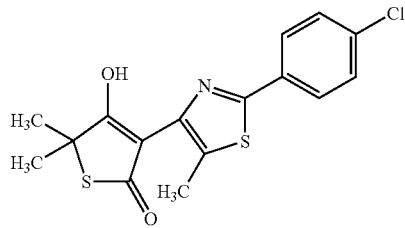

15 g (20 mmol) of the compound according to Example (IV-A-1) are initially charged in 22 ml of trifluoroacetic acid (TFA) and 51 ml of toluene, and the mixture is heated at reflux overnight. The solvent and the TFA are distilled off and the residue is taken up in 200 ml of water and 200 ml of methyl tert-butyl ether. The organic phase is extracted with alkali, the aqueous phase is acidified and extracted with dichloromethane, the organic extract is dried and the solvent is distilled off.

The residue is purified by silica gel column chromatography (dichloromethane/ethyl acetate, 10:1→5:1).

Yield: 1.6 g (23% of theory), m.p. 132–135° C.

Example I-3-A-c-1

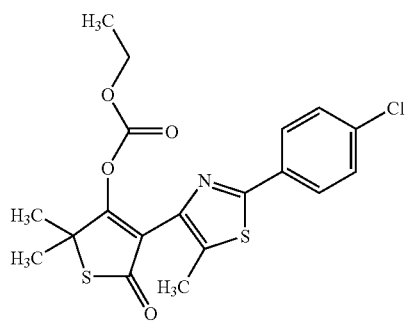

500 mg (1.4 mmol) of the compound according to Example (I-3-A-a-1) are initially charged in 5 ml of absolute dichloromethane and mixed with 0.29 ml (2.1 mmol, 1.5 eq) of triethylamine, and 0.2 g (1.8 mmol, 1.3 eq) of ethyl chloroformate are added with ice-cooling.

The mixture is stirred at room temperature for 2 hours, washed with 10% strength citric acid, extracted with dichloromethane, washed with 1 N NaOH and extracted with dichloromethane. The extract is dried and the solvent is distilled off.

Yield: 0.55 g (93% of theory) oil.

$^1$H-NMR (d$_6$-DMSO, 400 MHz): δ=0.93 (t, 3H, C$\underline{H_3}$—CH$_2$), 1.75 (s, 6H, 2 C$\underline{H_3}$—C), 2.37 (s, 3H, CH$_3$—C arom.), 3.98 (q, 2H, CH$_3$—C$\underline{H_2}$), 7.55 (d, 2H, 2 CH arom.), 7.87 (d, 2H, 2 CH arom.) ppm.

Example IV-A-1

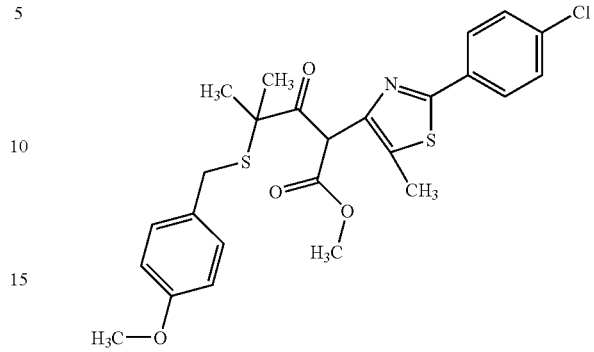

4.8 g (20.0 mmol) of 2-(4-methoxy-benzylthio)-2-methyl-propionic acid are initially charged in 40 ml of anhydrous toluene and 1 drop of DMF, and 7.2 g (60 mmol, 4 ml) of thionyl chloride are added. The mixture is stirred at room temperature for 5 min and then at 100° C. until evolution of gas has ceased. The solvent is distilled off and the residue is taken up in 10 ml of anhydrous tetrahydrofuran (solution A).

17.1 ml of lithium diisopropylamide are initially charged at 0° C. in 40 ml of anhydrous tetrahydrofuran, and 10.1 g (32.7 mmol) of methyl 4-[5-methyl-2-(4-chloro-phenyl)]-thiazolylacetate in 10 ml of anhydrous tetrahydrofuran are added dropwise at 0° C., and the mixture is stirred for another 30 min. Solution A is then added dropwise at 0° C., and the mixture is stirred at room temperature for 1 h. The reaction mixture is then admixed with 100 ml of MTB ether and a few drops of water and washed 2× with in each case 100 ml of 10% strength NH$_4$Cl solution. The organic phase is dried and the solvent is distilled off. The crude product is reacted without further purification.

Yield: 15.2 g (100% of theory).

$^1$H-NMR (DMSO, 400 MHz): δ=1.43 (s, 3H, C$\underline{H_3}$—C aliph.), 1.50 (s, 3H, C$\underline{H_3}$—C aliph.), 2.40 (s, 3H, C$\underline{H_3}$—C heteroatom.), 3.31 (s, 2H, CH$_2$), 3.61 (s, 3H, CH$_3$—OCO), 3.82 (s, 3H, CH$_3$—O) ppm.

Example XVI-1

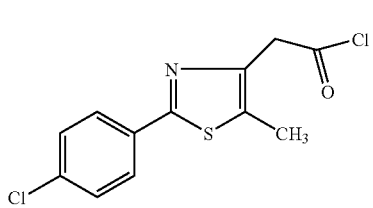

3 g (11.21 mmol) of 4-[2-(4-chlorophenyl)-5-methyl]-thiazolyl-acetic acid are initially charged in 50 ml of absolute dichloromethane. With ice-cooling, 2.13 g (16.81 mmol) of oxalyl chloride are slowly added dropwise, the mixture is stirred at room temperature overnight and then heated at reflux for 2 h, and the solvent is distilled off.

Yield: 3.19 g (96% of theory).

Example I-1-B-a-1

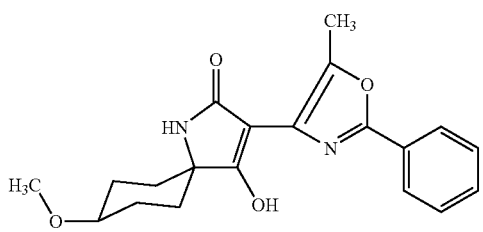

Example II-B-1

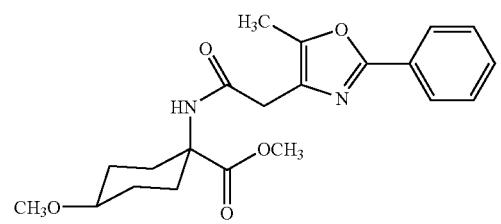

At 20° C., 3.59 g of the compound according to Preparation Example II-B-1 in 7 ml of anhydrous DMF are added dropwise to 2.41 g (0.020 mol) of potassium tert-butoxide in 17 ml of anhydrous dimethylformamide (DMF), and the mixture is stirred at 40° C. for 1 hour.

The reaction solution is stirred into 100 ml of ice-water and, at from 0 to 10° C., acidified with hydrochloric acid. The precipitate is filtered off with suction and chromatographed on silica gel using methylene chloride/acetone 5:1.

Yield: 1.2 g (36% of theory), m.p. >240° C.

The following compounds of the formula (I-1-B-a) are obtained similarly to Example (I-1-B-a-1) and in accordance with the general statements on the preparation 4.56 g (20 mmol) of methyl 1-amino-4-methoxy-cyclohexanecarboxylate hydrochloride are initially charged in 60 ml of absolute THF, admixed with 6 ml of triethylamine and stirred for 5 min. 3.27 g of 4-(2-phenyl-5-methyl)-oxazolyl-acetic acid are added, and the mixture is stirred at room temperature for 15 min. 3.3 ml of triethylamine are added and 0.84 ml of phosphorus oxychloride is added dropwise such that the solution boils moderately.

The mixture is stirred at reflux for 30 min.

The solvent is distilled off and the precipitate is purified by silica gel column chromatography (dichloromethane/ethyl acetate, 3:1).

Yield: 3.5 g (61% of theory), m.p. 125° C.

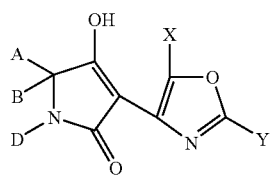

(I-1-B-a)

| Ex. No. | X | Y | D | A | B | m.p.° C. | isomer |
|---|---|---|---|---|---|---|---|
| I-1-B-a-2 | $CH_3$ | $C_6H_6$ | H | $CH_3$ | $CH_3$ | 187 | — |
| I-1-B-a-3 | $CH_3$ | 4-Cl—$C_6H_4$ | H | —$(CH_2)_2$—$CHOCH_3$—$(CH_2)_2$— | | 279 | β |

The following compounds of the formula (II-B) are obtained similarly to Example (II-B-1) and in accordance with the general statements on the preparation

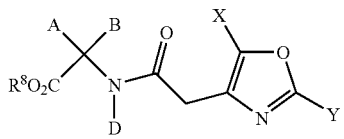

(II-B)

| Ex. No. | X | Y | D | A | B | $R^8$ | m.p.° C. | isomer |
|---|---|---|---|---|---|---|---|---|
| II-B-2 | $CH_3$ | $C_6H_5$ | H | $CH_3$ | $CH_3$ | $CH_3$ | 101 | — |
| II-B-3 | $CH_3$ | 4-Cl—$C_6H_4$ | H | —$(CH_2)_2$—$CHOCH_3$—$(CH_2)_2$— | | $CH_3$ | 95 | β |

Example I-2-B-a-1

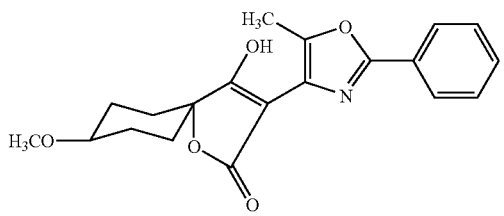

In the absence of a solvent, 1.01 g (5 mmol) of ethyl 4-methoxy-1-hydroxy-cyclohexane-1-carboxylate and 1.095 g (5 mmol) of 2-phenyl-4-methyl-isoxazol-3-acetyl chloride were heated at 140° C. overnight and then briefly degassed under reduced pressure. The resulting crude product was dissolved in 10 ml of DMF. 6 ml of a 1M solution of KOtBu in DMF were metered in over a period of 10 min, the mixture was stirred at room temperature overnight and then evaporated to dryness using a rotary evaporator, the residue was dissolved in water and extracted 1× with ethyl acetate to remove impurities, 10 ml of 1N hydrochloric acid were slowly metered in (until the mixture was acidic) and the precipitated product was filtered off with suction. Further purification was carried out by preparative HPLC (acetonitrile/water on RP-18):

Yield: 0.33 g (19% of theory), m.p. 65° C.

$^1$H-NMR MHz (CDCl$_3$): δ=1.60–2.30 (m, 8H), 2.85 (s, 3H), 3.30/3.40 (2s, 3H), 3.30/3.60 (2 m, 1H), 7.40–8.00 (m, 5H).

The following compounds of the formula (I-2-B-a) are obtained similarly to Example (I-2-B-a-1) and in accordance with the general statements on the preparation (I-2-B-a)

| Ex. No. | X | Y | A | B | m.p.° C. |
|---|---|---|---|---|---|
| I-2-B-a-2 | CH$_3$ | C$_6$H$_5$ | CH$_3$ | CH$_3$ | log P $_{(pH2)}$ 3.43 |

Use Examples

Example A

| Meloidogyne test | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action in % is determined using the formation of galls as a measure. 100% means that no galls have been found; 0% means that the number of galls on the treated plants corresponds to that on the untreated control.

In this test, for example, the following compounds of the Preparation Examples show good activity: I-2-A-a-1 and I-2-A-a-2.

Example B

| Myzus test | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: I-2-A-a-1, I-1-A-a-5, I-1-A-a-6 and I-1-A-a-8.

Example C

| Phaedon larvae test | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with the larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity: I-2-A-a-1, I-2-A-a-2, I-1-A-a-3, I-1-A-a-4, I-1-A-a-5, I-1-A-a-6, I-1-A-a-2, I-1-A-a-1, I-1-A-c-1 and I-1-A-a-8.

Example D

| Spodoptera frugiperda test | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples showed good activity: I-2-A-a-1, I-1-A-a-4, I-1-A-a-5, I-1-A-a-6, I-1-A-a-2, I-1-A-a-1 and I-1-A-c-1.

Example E

*Tetranychus* test (OP-resistant/dip treatment)

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed. 0% means that none of the spider mites have been killed.

In this test, for example, the following compounds of the Preparation Examples show good activity: I-2-A-a-2, I-1-A-a-4, I-1-A-a-5 and I-1-A-a-6.

Example F

Post-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5 to 15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

| 0% = | no effect (like untreated control) |
|---|---|
| 100% = | total destruction |

Example G

Pre-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0% = no effect (like untreated control)
100% = total destruction

| pre-emergence | g ai/ha | sugar beet | oilseed rape | Alopecurus | Avena fatua | Lolium | Setaria | Matricaria |
|---|---|---|---|---|---|---|---|---|
| Ex. I-2-a-1 | 125 | 0 | 0 | 90 | 100 | 100 | 100 | 100 |

| post-emergence | g ai/ha | oilseed rape | Alopecurus | Avena Fatua | Echinochloa | Setaria | Amaranthus | Chenopodium |
|---|---|---|---|---|---|---|---|---|
| Ex. I-2-a-1 | 250 | 20 | 80 | 95 | 100 | 100 | 70 | 70 |

-continued

| pre-emergence | g ai/ha | sugar beet | oilseed rape | Avena fatua | Bromus | Lolium | Setaria |
|---|---|---|---|---|---|---|---|
| Ex. I-2-a-2 | 250 | 0 | 0 | 90 | 90 | 100 | 100 |

| post-emergence | g ai/ha | sugar beet | Soya bean | Avena fatua | Digitaria | Echinochloa | Setaria |
|---|---|---|---|---|---|---|---|
| Ex. I-2-a-2 | 250 | 0 | 0 | 90 | 90 | 100 | 95 |

| post-emergence | g ai/ha | Alopecurus | Echinochloa | Amaranthus |
|---|---|---|---|---|
| Ex. I-1-a-5 | 250 | 80 | 100 | 90 |

| post-emergence | g ai/ha | sugar beet | Alopecurus | Avena fatua | Digitaria | Echinochloa |
|---|---|---|---|---|---|---|
| Ex. I-1-a-6 | 125 | 0 | 90 | 90 | 95 | 90 |

| post-emergence | g ai/ha | Alopecurus | Echinochloa | Setaria | Amaranthus |
|---|---|---|---|---|---|
| Ex. I-1-a-2 | 250 | 70 | 90 | 95 | 90 |

| post-emergence | g ai/ha | Alopecurus | Avena fatua | Echinochloa | Amaranthus | Sinapis |
|---|---|---|---|---|---|---|
| Ex. I-1-a-1 | 250 | 80 | 80 | 95 | 70 | 80 |

| post-emergence | g ai/ha | rice | Avena fatua | Digitaria | Echinochloa | Stellaria |
|---|---|---|---|---|---|---|
| Ex. I-1-a-3 | 250 | 10 | 100 | 100 | 100 | 90 |

| post-emergence | g ai/ha | Alopecurus | Avena fatua | Echinochloa | Setaria |
|---|---|---|---|---|---|
| Ex. I-1-c-1 | 250 | 80 | 95 | 95 | 90 |

| post-emergence | g ai/ha | Alopecurus | Avena fatua | Echinochloa | Setaria | Abutilon | Amaranthus |
|---|---|---|---|---|---|---|---|
| Ex. I-1-a-4 | 250 | 95 | 100 | 100 | 100 | 80 | 95 |
| Ex. I-1-b-1 | 250 | 95 | 100 | 100 | 100 | 80 | 80 |

Example H

Critical Concentration Test/Soil Insects—Treatment of Transgenic Plants

| Test insect: *Diabrotica balteata* - Larvae in soil | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the variety YIELD GUARD (trademark of Monsanto Comp., USA) are placed into each pot. After 2 days, the test insects concerned are placed into the treated soil. After a further 7 days, the efficacy of the active compound is determined by counting the maize plants that have emerged (1 plant=20% efficacy).

Example I

| *Heliothis virescens* test - treatment of transgenic plants | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the variety Roundup Ready (trademark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

The invention claimed is:
1. A compound of the formula (I)

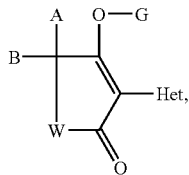 (I)

in which
W represents oxygen,
Het represents optionally substituted thiazolyl having the formula

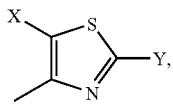

in which
X represents hydrogen, halogen, $C_1$–$C_6$-alkyl, $C_1$–$C_4$-halogenoalkyl, $C_1$–$C_6$-alkoxy, $C_3$–$C_6$-alkenyloxy, nitro, or cyano, and
Y represents a group

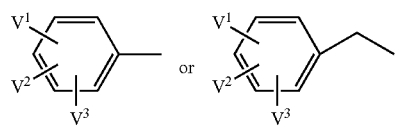

in which
$V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano, or phenoxy; or represents phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro, or cyano, and
$V^2$ and $V^3$ independently of one another each represent hydrogen, halogen, $C_1$–$C_6$-alkyl, $C_1$–$C_6$-alkoxy, $C_1$–$C_4$-halogenoalkyl, or $C_1$–$C_4$-halogenoalkoxy, or
$V^1$ and $V^2$ together with the carbon atoms to which they are attached represent an optionally $C_1$–$C_4$-alkyl- or halogen-substituted saturated or unsaturated 5- or 6-membered cycle,
A represents hydrogen; optionally halogen-substituted alkyl, alkenyl, alkoxyalkyl, polyalkoxyalkyl, alkylthioalkyl, or saturated or unsaturated cycloalkyl; or optionally halogen-, alkyl-, halogenoalkyl, alkoxy-, halogenoalkoxy-, cyano- or nitro- substituted aryl or arylalkyl,
B represents hydrogen, alkyl or alkoxyalkyl, or
A and B together with the carbon atom to which they are attached represent a saturated or unsaturated unsubstituted or substituted cycle, and
G represents hydrogen (a) or one of the groups

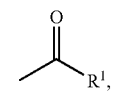 (b)

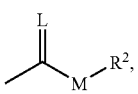 (c)

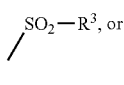 (d)

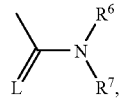 (g)

in which
L represents oxygen or sulphur,
M represents oxygen or sulphur,
$R^1$ represents optionally halogen-substituted alkyl, alkenyl, alkoxyalkyl, alkylthioalkyl, or polyalkoxyalkyl; represents optionally halogen-, alkyl-, or alkoxy-substituted cycloalkyl; or represents optionally substituted phenyl, phenylalkyl, hetaryl, or phenoxyalkyl,
$R^2$ represents optionally halogen-substituted alkyl, alkenyl, alkoxyalkyl, or polyalkoxyalkyl; or represents optionally substituted cycloalkyl, phenyl, or benzyl,
$R^3$ represents alkyl or halogenoalkyl; or represents optionally substituted phenyl or benzyl, and
$R^6$ and $R^7$ independently of one another each represents hydrogen; represents optionally halogen-substituted alkyl, cycloalkyl, alkenyl, alkoxy, or alkoxyalkyl; represents optionally substituted phenyl; or represents optionally substituted benzyl; or $R^6$ and $R^7$ together with the N atom to which they are attached represent a cycle.

2. A compound of the formula (I) according to claim 1 in which
Het represents

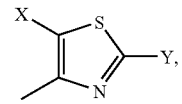

X represents hydrogen, halogen, $C_1$–$C_6$-alkyl, $C_1$–$C_4$-halogenoalkyl, $C_1$–$C_6$-alkoxy, $C_3$–$C_6$-alkenyloxy, nitro, or cyano,
Y represents a group

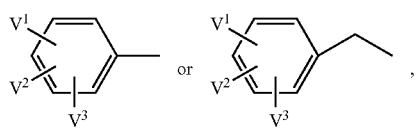

in which
$V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano, or phenoxy; or represents phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro, or cyano, and $V^2$ and $V^3$ independently of one another each represent hydrogen, halogen, $C_1$–$C_6$-alkyl, $C_1$–$C_6$-alkoxy, $C_1$–$C_4$-halogenoalkyl, or $C_1$–$C_4$-halogenoalkoxy, or $V^1$ and $V^2$ together with the carbon atoms to which they are attached represent an optionally $C_1$–$C_4$-alkyl- or halogen-substituted saturated or unsaturated 5- or 6-membered cycle, W represents oxygen, A represents hydrogen; optionally fluorine- or chlorine-substituted $C_1$–$C_{12}$-alkyl, $C_3$–$C_8$-alkenyl, $C_1$–$C_6$-alkoxy-$C_1$–$C_6$-alkyl, poly-$C_1$–$C_6$-alkoxy-$C_1$–$C_6$-alkyl, or $C_1$–$C_{10}$-alkylthio-$C_1$–$C_6$-alkyl; optionally fluorine-, chlorine-, $C_1$–$C_6$-alkyl- or $C_1$–$C_6$-alkoxy-substituted $C_3$–$C_8$-cycloalkyl; or optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano-, or nitro-substituted $C_6$- or $C_{10}$-aryl or $C_6$- or $C_{10}$-aryl-$C_1$–$C_6$-alkyl, B represents hydrogen, $C_1$–$C_6$-alkyl or $C_1$–$C_4$-alkoxy-$C_1$–$C_4$-alkyl, or A, B, and the carbon atom to which they are attached represent saturated $C_3$–$C_{10}$-cycloalkyl or unsaturated $C_5$–$C_{10}$-cycloalkyl that are optionally mono- or disubstituted by $C_1$–$C_6$-alkyl, $C_3$–$C_8$-cycloalkyl, $C_1$–$C_4$-halogenoalkyl, $C_1$–$C_6$-alkoxy, $C_1$–$C_6$-alkylthio, halogen, or phenyl, or A, B, and the carbon atom to which they are attached represent $C_5$–$C_6$-cycloalkyl that is substituted by an alkylenediyl group, or A, B, and the carbon atom to which they are attached represent $C_3$–$C_8$-cycloalkyl or $C_5$–$C_8$-cycloalkenyl in which two substituents together with the carbon atoms to which they are attached represent optionally $C_1$–$C_6$-alkyl-, $C_1$–$C_6$-alkoxy-, or halogen-substituted $C_2$–$C_6$-alkanediyl, $C_2$–$C_6$-alkenediyl, or $C_4$–$C_6$-alkanedienediyl, and G represents hydrogen (a) or one of the groups

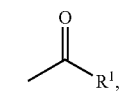
(b)

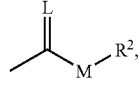
(c)

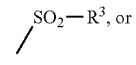
(d)

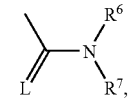
(g)

in which

L represents oxygen or sulphur,

M represents oxygen or sulphur, $R^1$ represents optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl, or optionally halogen-, $C_1$–$C_6$-alkyl- or $C_1$–$C_6$-alkoxy-substituted $C_3$–$C_8$-cycloalkyl; represents optionally halogen-, cyano-, nitro-, $C_1$–$C_6$-alkyl, $C_1$–$C_6$-alkoxy-, $C_1$–$C_6$-halogenoalkyl-, $C_1$–$C_6$-halogenoalkoxy-, $C_1$–$C_6$-alkylthio-, or $C_1$–$C_6$-alkylsulphonyl-substituted phenyl; or represents optionally halogen-, nitro-, cyano-, $C_1$–$C_6$-alkyl-, $C_1$–$C_6$-alkoxy-, $C_1$–$C_6$-halogenoalkyl-, or $C_1$–$C_6$-halogenoalkoxy-substituted phenyl-$C_1$–$C_6$-alkyl; represents optionally halogen- or $C_1$–$C_6$-alkyl-substituted phenoxy-$C_1$–$C_6$-alkyl; or represents optionally halogen-, amino- or $C_1$–$C_6$-alkyl-substituted 5- or 6-membered hetaryloxy-$C_1$–$C_6$-alkyl, $R^2$ represents optionally halogen-substituted $C_1$–$C_{20}$-alkyl, $C_2$–$C_{20}$-alkenyl, $C_1$–$C_8$-alkoxy-$C_2$–$C_8$-alkyl, or poly-$C_1$–$C_8$-alkoxy-$C_2$–$C_8$-alkyl; represents optionally halogen-, $C_1$–$C_6$-alkyl, or $C_1$–$C_6$-alkoxy-substituted $C_3$–$C_8$-cycloalkyl; or represents optionally halogen-, cyano-, nitro-, $C_1$–$C_6$-alkyl-, $C_1$–$C_6$-alkoxy-, $C_1$–$C_6$-halogenoalkyl-, or $C_1$–$C_6$-halogenoalkoxy-substituted phenyl or benzyl, $R^3$ represents optionally halogen-substituted $C_1$–$C_8$-alkyl or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano-, or nitro-substituted phenyl or benzyl, and $R^6$ and $R^7$ independently of one another each represent hydrogen; represent optionally halogen-substituted $C_1$–$C_8$-alkyl, $C_3$–$C_8$-cycloalkyl, $C_1$–$C_8$-alkoxy, $C_3$–$C_8$-alkenyl, or $C_1$–$C_8$-alkoxy-$C_1$–$C_8$-alkyl; represent optionally halogen-, $C_1$–$C_8$-halogenoalkyl-, $C_1$–$C_8$-alkyl-, or $C_1$–$C_8$-alkoxy-substituted phenyl; represent optionally halogen-, $C_1$–$C_8$-alkyl-, $C_1$–$C_8$-halogenoalkyl-, or $C_1$–$C_8$-alkoxy-substituted benzyl; or $R^6$ and $R^7$ together represent an optionally $C_1$–$C_4$-alkyl-substituted $C_3$–$C_6$-alkylene radical.

3. A compound of the formula (I) according to claim 1 in which

Het represents

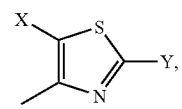

X represents hydrogen, chlorine, bromine, $C_1$–$C_4$-alkyl, $C_1$–$C_2$-halogenoalkyl, nitro, or cyano, Y represents a group

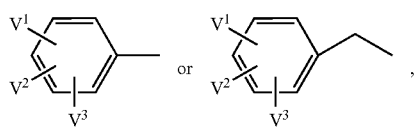

in which $V^1$ represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenoalkoxy, nitro, cyano, or phenoxy; or represents phenyl, phenoxy, phenoxy-$C_1$–$C_2$-alkyl, phenyl-$C_1$–$C_2$-alkoxy, phenylthio-$C_1$–$C_2$-alkyl, or phenyl-$C_1$–$C_2$-alkylthio, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro, or cyano, and $V^2$ represents hydrogen, fluorine, chlorine, bromine, $C_1$–$C_4$-alkyl, $C_1$–$C_4$-alkoxy, $C_1$–$C_2$-halogenoalkyl, or $C_1$–$C_2$-halogenoalkoxy, or $V^1$ and $V^2$ together with the carbon atoms to which they are attached represent an optionally fluorine- or methyl-substituted 5- or 6-membered cycle, W represents oxygen, A represents hydrogen; optionally fluorine-substituted $C_1$–$C_{10}$-alkyl or $C_1$–$C_4$-alkoxy-$C_1$–$C_4$-alkyl; optionally fluorine-, chlorine-, $C_1$–$C_4$-alkyl-, or $C_1$–$C_4$-alkoxy-substituted $C_3$–$C_7$-cycloalkyl; or optionally fluorine-, chlorine-, bromine-, $C_1$–$C_4$-alkyl-, $C_1$–$C_4$-halogenoalkyl-, $C_1$–$C_4$-alkoxy-, or $C_1$–$C_4$-halegenoalkoxy-substituted phenyl or phenyl-$C_1$–$C_2$-alkyl, B represents hydrogen or $C_1$–$C_4$-alkyl, or A, B, and the carbon atom to which they are attached represent saturated $C_5$–$C_7$-cycloalkyl that is optionally mono- or disubstituted by $C_1$–$C_6$-alkyl, $C_5$–$C_6$-cycloalkyl, $C_1$–$C_2$-halogenoalkyl, $C_1$–$C_6$-alkoxy, fluorine, chlorine, or phenyl, or A, B, and the carbon atom to which they are attached represent $C_5$–$C_6$-cycloalkyl that is substituted by an alkylenediyl group, or A, B, and the carbon atom to which they are attached represent $C_5$–$C_6$-cycloalkyl or $C_5$–$C_6$-cycloalkenyl in which two substituents together with the carbon atoms to which they are attached represent optionally $C_1$–$C_5$-alkyl-, $C_1$–$C_5$-alkoxy-, fluorine-, chlorine-, or bromine-substituted $C_2$–$C_4$-alkanediyl, $C_2$–$C_4$-alkenediyl, or butadienediyl, and G represents hydrogen (a) or one of the groups (b)

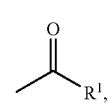

(c)

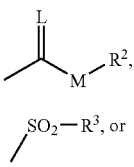

(d)

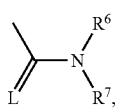

(g)

in which

L represents oxygen or sulphur,

M represents oxygen or sulphur, $R^1$ represents optionally fluorine- or chlorine-substituted $C_1$–$C_{16}$-alkyl, $C_2$–$C_{16}$-alkenyl, $C_1$–$C_6$-alkoxy-$C_1$–$C_4$-alkyl, or $C_1$–$C_6$-alkylthio-$C_1$–$C_4$-alkyl, or optionally fluorine-, chlorine-, $C_1$–$C_5$-alkyl-, or $C_1$–$C_5$-alkoxy-substituted $C_3$–$C_7$-cycloalkyl; represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio-, or $C_1$–$C_4$-alkylsulphonyl-substituted phenyl; or represents optionally fluorine-, chlorine-, bromine-, $C_1$–$C_4$-alkyl-, $C_1$–$C_4$-alkoxy-, $C_1$–$C_3$-halogenoalkyl-, or $C_1$–$C_3$-halogenoalkoxy-substituted phenyl-$C_1$–$C_4$-alkyl;

$R^2$ represents optionally fluorine-substituted $C_1$–$C_{16}$-alkyl, $C_2$–$C_{16}$-alkenyl, or $C_1$–$C_6$-alkoxy-$C_2$–$C_6$-alkyl; represents optionally fluorine-, chlorine-, $C_1$–$C_4$-alkyl-, or $C_1$–$C_4$-alkoxy-substituted $C_3$–$C_7$-cycloalkyl; or represents optionally fluorine-, chlorine-, bromine-, cyano-, nitro-, $C_1$–$C_4$-alkyl-, $C_1$–$C_3$-alkoxy-, $C_1$–$C_2$-halogenoalkyl-, or $C_1$–$C_2$-halogenoalkoxy-substituted phenyl or benzyl, $R^3$ represents optionally fluorine-substituted $C_1$–$C_6$-alkyl; or represents optionally fluorine-, chlorine-, bromine-, $C_1$–$C_4$-alkyl-, $C_1$–$C_4$-alkoxy-, $C_1$–$C_3$-halogenoalkyl-, $C_1$–$C_3$-halogenoalkoxy-, cyano-, or nitro- substituted phenyl, $R^6$ represents $C_1$–$C_6$-alkyl, $C_3$–$C_6$-cycloalkyl, $C_1$–$C_6$-alkoxy, $C_3$–$C_6$-alkenyl, or $C_1$–$C_6$-alkoxy-$C_1$–$C_6$-alkyl; represents optionally fluorine-, chlorine-, bromine-, $C_1$–$C_3$-halogenoalkyl-, $C_1$–$C_4$-alkyl-, or $C_1$-$C_4$- alkoxy-substituted phenyl; or represents optionally fluorine-, chlorine-, bromine-, $C_1$–$C_4$-alkyl-, $C_1$–$C_3$-halogenoalkyl-, or $C_1$–$C_4$-alkoxy-substituted benzyl, and $R^7$ represents hydrogen, $C_1$–$C_6$-alkyl, or $C_3$–$C_6$-alkenyl, or $R^6$ and $R^7$ together represent an optionally methyl- or ethyl-substituted $C_4$–$C_5$-alkylene radical.

4. A compound of the formula (I) according to claim 1 in which

Het represents

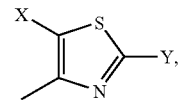

X represents hydrogen, chlorine, bromine, methyl, ethyl, n-propyl, iso-propyl, n-butyl, or iso-butyl, Y represents a group

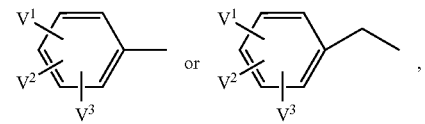

in which $V^1$ represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano, phenoxy, or phenyl that is optionally mono- or disubstituted by fluorine, chlorine, methyl, methoxy, trifluoromethyl, or trifluoromethoxy, and $V^2$ represents hydrogen, fluorine, chlorine, methyl, ethyl, n-propyl, iso-propyl, methoxy, ethoxy, trifluoromethyl, or trifluoromethoxy, W represents oxygen, A represents hydrogen; represents optionally fluorine-substituted $C_1$–$C_8$-alkyl or $C_1$–$C_4$-alkoxy-$C_1$–$C_2$-alkyl; or represents optionally fluorine-, methyl-, ethyl-, or methoxy-substituted $C_3$–$C_6$-cycloalkyl, B represents hydrogen, methyl, or ethyl, or A, B, and the carbon atom to which they are attached represent saturated $C_5$–$C_6$-cycloalkyl that is optionally mono- or disubstituted by methyl, ethyl, propyl, iso-propyl, butyl, isobutyl, sec-butyl, tert-butyl, trifluoromethyl, methoxy, ethoxy, propoxy, iso-propoxy, butoxy, or iso-butoxy, or A, B, and the carbon atom to which they are attached represent $C_5$–$C_6$-cycloalkyl or $C_5$–$C_6$-cycloalkenyl in which two substituents together with the carbon atoms to which they are attached represent $C_2$–$C_4$-alkanediyl or $C_2$–$C_4$-alkenediyl in which one methylene group is optionally replaced by oxygen or sulphur, or represent butadienediyl, and G represents hydrogen (a) or one of the groups

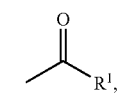
(b)

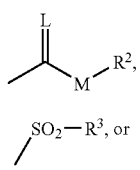
(c)

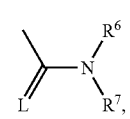
(d)

(g)

in which

L represents oxygen or sulphur,

M represents oxygen or sulphur, $R^1$ represents optionally fluorine-substituted $C_1$–$C_{14}$-alkyl, $C_2$–$C_{14}$-alkenyl, $C_1$–$C_4$-alkoxy-$C_1$–$C_2$-alkyl, or $C_1$–$C_4$-alkylthio-$C_1$–$C_2$-alkyl, or optionally fluorine-, chlorine-, methyl-, ethyl- or methoxy-substituted cyclopropyl, cyclopentyl, or cyclohexyl; or represents phenyl that is optionally mono- or disubstituted by fluorine, chlorine, bromine, cyano, nitro, methyl, ethyl, tert-butyl, methoxy, ethoxy, trifluoromethyl, or trifluoromethoxy;

$R^2$ represents optionally fluorine-substituted $C_1$–$C_8$-alkyl, $C_2$–$C_8$-alkenyl, or $C_1$–$C_4$-alkoxy-$C_2$–$C_3$-alkyl; represents optionally fluorine-, chlorine-, methyl-, ethyl-, n-propyl-, iso-propyl-, or methoxy-substituted cyclo hexyl; or represents optionally fluorine-, chlorine-, cyano-, nitro-, methyl-, ethyl-, methoxy-, trifluoromethyl-, or trifluoromethoxy-substituted phenyl or benzyl, $R^3$ represents methyl, ethyl, or n-propyl; or represents phenyl that is optionally monosubstituted by fluorine, chlorine, bromine, methyl, tert-butyl, methoxy, trifluoromethyl, trifluoromethoxy, cyano, or nitro, $R^6$ represents $C_1$–$C_4$-alkyl, $C_3$–$C_6$-cycloalkyl, $C_1$–$C_4$-alkoxy, $C_3$–$C_4$-alkenyl, or $C_1$–$C_4$-alkoxy-$C_1$–$C_4$-alkyl; represents optionally fluorine-, chlorine-, bromine-, trifluoromethyl-, methyl-, or methoxy-substituted phenyl; represents optionally fluorine-, chlorine-, bromine-, methyl-, trifluoromethyl-, or methoxy-substituted benzyl, and $R^7$ represents hydrogen, methyl, ethyl, propyl, or allyl, or $R^6$ and $R^7$ together represent a $C_5$–$C_6$-alkylene radical.

5. A compound of the formula (I) according to claim 1 in which

Het represents

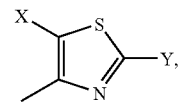

X represents hydrogen, chlorine, bromine, methyl, ethyl, n-propyl, or iso-propyl, Y represents a group

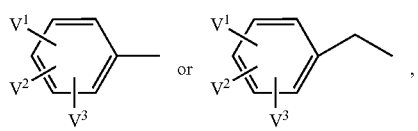

in which $V^1$ represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, or phenoxy; or represents optionally chlorine- or trifluoromethyl-substituted phenyl, and $V^2$ represents hydrogen, fluorine, chlorine, methyl, ethyl, methoxy, or trifluoromethyl, W represents oxygen, A represents hydrogen, $C_1$–$C_4$-alkyl, or cyclopropyl, B represents hydrogen or methyl, or A, B, and the carbon atom to which they are attached represent saturated $C_5$–$C_6$-cycloalkyl that is optionally mono- or disubstituted by methyl, ethyl, propyl, iso-propyl, trifluoromethyl, methoxy, ethoxy, propoxy, butoxy, or iso-butoxy; or represents $C_5$–$C_6$-cycloalkyl in which two carbon atoms that are not directly adjacent form a further five-membered ring, and G represents hydrogen (a) or when Het is thiazolyl (A) represents one of the groups

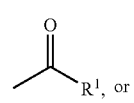
(b)

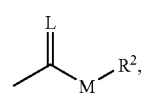
(c)

in which

L represents oxygen,

M represents oxygen, $R^1$ represents optionally fluorine- or chlorine-substituted $C_1$–$C_4$-alkyl, $C_2$–$C_4$-alkenyl, $C_1$–$C_4$-alkoxy-$C_1$–$C_2$-alkyl, or $C_1$–$C_4$-alkylthio-$C_1$–$C_2$-alkyl, or optionally fluorine-, chlorine-, methyl-, ethyl-, or methoxy- substituted cyclopropyl or cyclohexyl; or represents phenyl that is optionally monosubstituted by fluorine, chlorine, bromine, cyano, nitro, methyl, ethyl, n-propyl, i-propyl, tert-butyl, methoxy, ethoxy, i-propoxy, tert-butoxy, trifluoromethyl, or trifluoromethoxy; and $R^2$ represents optionally fluorine-substituted $C_1$–$C_4$-alkyl, $C_2$–$C_4$-alkenyl, or $C_1$–$C_4$-alkoxy-$C_2$–$C_3$-alkyl; represents optionally methyl-, ethyl-, n-propyl-, iso-propyl-, or methoxy-substituted cyclohexyl; or represents phenyl or benzyl, each of which is optionally monosubstituted by fluorine, chlorine, cyano, nitro, methyl, ethyl, methoxy, trifluoromethyl, or trifluoromethoxy.

6. A compound of the formula (I) according to claim 1 in which

Het represents

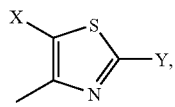

X represents methyl, ethyl, n-propyl, i-propyl, chlorine, or bromine,

Y represents the groups

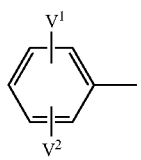 or 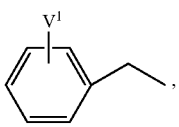, in which $V^1$ represents hydrogen, bromine, chlorine, methyl, trifluoromethyl, phenoxy, or t-butyl; or represents optionally chlorine- or trifluoromethyl-substituted phenyl, and $V^2$ represents hydrogen, chlorine, fluorine, or methoxy, W represents oxygen, A represents methyl, ethyl, n- or i-propyl, cyclopropyl, or hydrogen, B represents hydrogen or methyl, or A and B and the carbon atom to which they are attached represent cyclohexyl that is optionally mono- or disubstituted by methyl, ethyl, methoxy, or ethoxy; or represent cyclohexyl in which two carbon atoms that are not directly adjacent form a further 5-membered C ring, and G represents hydrogen (a) or one of the groups

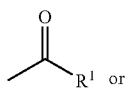   (b)

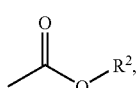,   (c)

in which $R^1$ represents methyl, ethyl, n-propyl, or i-propyl; or represents optionally chlorine-substituted phenyl, and $R^2$ represents methyl, ethyl, phenyl, benzyl, or n- or i-propyl.

7. A compound of the formula (I) according to claim 1 in which

Het represents

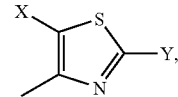

X represents methyl or ethyl,

Y represents optionally chlorine-substituted phenyl,

A represents methyl, ethyl, or n- or i-propyl,

B represents methyl, or

A and B and the carbon atom to which they are attached together represent cyclohexyl that is optionally substituted by methoxy or methyl, W represents oxygen, and G represents hydrogen (a) or one of the groups

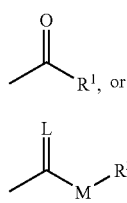   (b)

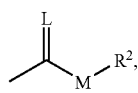   (c)

in which $R^1$ represents methyl, ethyl, n-propyl, or i-propyl; or represents optionally chlorine-substituted phenyl, and $R^2$ represents methyl, ethyl, phenyl, benzyl, or n- or i-propyl.

8. A process for preparing compounds of the formula (I) according to claim 1 comprising intramolecularly condensing compounds of the formula (III)

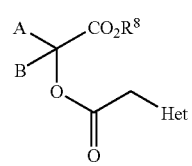   (III)

in which

A, B, and Het, are each as defined in claim 1, and $R^8$ represents alkyl, in the presence of a diluent and in the presence of a base, to obtain compounds of the formula (I-2-A-a)

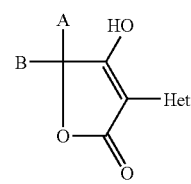   (I-2-A-a)

in which A, B and Het are each as defined in claim 1, and optionally further comprising reacting resulting compounds with (D) (α) an acyl halide of the formula (V)

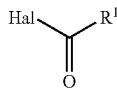
(V)

in which
R¹ is as defined in claim 1, and
Hal represents halogen,
or
(β) a carboxylic anhydride of the formula (VI)

$R^1$—CO—O—CO—$R^1$ (VI)

in which R¹ is as defined in claim 1, optionally in the presence of a diluent and optionally in the presence of an acid binder; or
(E) a chloroformic ester or chloroformic thioester of the formula (VII)

$R^2$-M-CO—Cl (VII)

in which $R^2$ and M are each as defined in claim 1, optionally in the presence of a diluent and optionally in the presence of an acid binder; or
(F) a chloromonothioformic ester or chlorodithioformic ester of the formula (VIII)

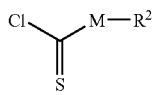
(VIII)

in which M and $R^2$ are each as defined in claim 1, optionally in the presence of a diluent and optionally in the presence of an acid binder; or (G) a sulphonyl chloride of the formula (IX)

$R^3$—SO₂—Cl (IX)

in which $R^3$ is as defined in claim 1, optionally in the presence of a diluent and optionally in the presence of an acid binder; or
(J) (α) an isocyanate or isothiocyanate of the formula (XIII)

$R^6$—N=C=L (XIII)

in which $R^6$ and L are each as defined in claim 1, optionally in the jpresence of a diluent and optionally in the presence of a catalyst; or
(β) a carbamoyl chloride or thiocarbamoyl chloride of the formula (XIV)

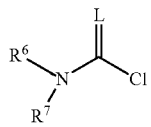
(XIV)

in which L, $R^6$, and $R^7$ are each as defined in claim 1, optionally in the presence of a diluent and optionally in the presence of an acid binder.

9. A pesticide comprising one or more compounds of the formula (I) according to claim 1 and one or more extenders and/or surfactants.

10. An herbicide comprising one or more compounds of the formula (I) according to claim 1 and one or more extenders and/or surfactants.

11. A method for controlling pests comprising allowing a pesticidally effective amount of a compound of the formula (I) according to claim 1 to act on the pests and/or their habitat.

\* \* \* \* \*